(12) United States Patent
Zheng et al.

(10) Patent No.: US 11,414,487 B2
(45) Date of Patent: Aug. 16, 2022

(54) MONOCLONAL ANTIBODIES TO PROGRAMMED DEATH 1 (PD-1)

(71) Applicants: CStone Pharmaceuticals, Grand Cayman (KY); CStone Pharmaceuticals (Suzhou) Co., Ltd., Suzhou (CN); CStone Pharmaceuticals (Shanghai) Co., Ltd., Shanghai (CN)

(72) Inventors: Yong Zheng, Shanghai (CN); Jing Li, Lexington, MA (US); Gennady Gololobov, Gaithersburg, MD (US); Xinhua Zhang, Shanghai (CN); Baotian Yang, Shanghai (CN); Zhewei Tang, Shanghai (CN); Dong Li, Shanghai (CN); Jianqing Xu, Shanghai (CN); Zhuozhi Wang, Millbrae, CA (US)

(73) Assignees: CStone Pharmaceuticals, Grand Cayman (KY); CStone Pharmaceuticals (Suzhou) Co., Ltd., Suzhou (CN); CStone Pharmaceuticals (Shanghai) Co., Ltd., Shanghai (CN)

( * ) Notice: Subject to any disclaimer, the term of this patent is extended or adjusted under 35 U.S.C. 154(b) by 270 days.

(21) Appl. No.: 16/333,993

(22) PCT Filed: Sep. 21, 2016

(86) PCT No.: PCT/CN2016/099576
§ 371 (c)(1),
(2) Date: Mar. 15, 2019

(87) PCT Pub. No.: WO2018/053709
PCT Pub. Date: Mar. 29, 2018

(65) Prior Publication Data
US 2020/0002420 A1 Jan. 2, 2020

(51) Int. Cl.
*C07K 16/28* (2006.01)
*A61P 35/00* (2006.01)
*C12N 15/63* (2006.01)

(52) U.S. Cl.
CPC ......... *C07K 16/2818* (2013.01); *A61P 35/00* (2018.01); *C07K 16/2806* (2013.01); *C07K 16/2809* (2013.01); *C12N 15/63* (2013.01)

(58) Field of Classification Search
CPC ............ C07K 16/2818; C07K 16/2806; C07K 16/2809; C12N 15/63
See application file for complete search history.

(56) References Cited

U.S. PATENT DOCUMENTS

| 8,168,757 | B2 | 5/2012 | Finnefrock et al. |
| 9,084,776 | B2 | 7/2015 | Korman et al. |
| 10,414,821 | B2 | 9/2019 | Liu |
| 11,008,391 | B2 * | 5/2021 | Zheng ............. A61P 35/00 |
| 2016/0159905 | A1 | 6/2016 | Abdiche et al. |
| 2019/0270815 | A1 * | 9/2019 | Zheng ............ C07K 16/2827 |
| 2020/0354460 | A1 * | 11/2020 | Wang ............... A61P 35/00 |

FOREIGN PATENT DOCUMENTS

| CA | 2955541 | A1 | 2/2016 |
| CN | 105330740 | B | 8/2018 |
| WO | 2006021955 | A2 | 3/2006 |
| WO | 2013148250 | A1 | 10/2013 |
| WO | 2015112900 | A1 | 7/2015 |
| WO | 2016/077397 | A2 | 5/2016 |
| WO | 2016/127179 | A2 | 8/2016 |
| WO | 2017025051 | A1 | 2/2017 |
| WO | 2017055547 | A1 | 4/2017 |

OTHER PUBLICATIONS

Wang et al., In Vitro Characterization of the Anti-PD-1 Antibody Nivolumab, BMS-936558, and In Vivo Toxicology in Non-Human Primates, Cancer Immunol Res, 2014, 2(9), 846-856, Publication Date: May 28, 2014 (Year: 2014).*
Almagro & Fransson, Humanization of antibodies, Frontiers in Bioscience 2008; 13: 1619-33 (Year: 2008).*
OPDIVO, Highlight of Prescribing Information, Reference ID: 3827356, Publication Date: Sep. 2015 (Year: 2015).*
Smaglo et al., The development of immunoconjugates for targeted cancer therapy, Nat. Rev. Clin. Oncol. 11, 637-648, Publication Date: Sep. 30, 2014 (Year: 2014).*
Wang, C., et al. "In Vitro characterization of the Anti-PD-1 Antibody Nivolumab, BMS-936558, and In Vivo Toxicology in Non-Human Primates." Cancer Immunol Res., vol. 2, No. 9, May 28, 2014 (May 28, 2014), pp. 846-856, 12 pages.
Ohaegbulam, K., et al. "Human cancer immunotherapy with antibodies to the PD-1 and PD-L1 pathway," Trends Mol Med., Jan. 2015, 21(1): 24-33. doi:10.1016/j.molmed.2014.10.009. 23 pages.
Hardy, B., et al. "Activation of human lymphocytes by a monoclonal antibody to B lymphoblastoid cells; molecular mass and distribution of binding protein," Cancer Immunol Immunother (1995) 40:376-382, Springer-Verlag, 1995, 7 pages.
International Search Report of International Patent Application No. PCT/CN2016/099576, dated Jun. 26, 2017, 5 pages.
Written Opinion of International Patent Application No. PCT/CN2016/099576, dated Jun. 26, 2017, 7 pages.
International Preliminary Report on Patentability of International Patent Application No. PCT/CN2016/099576, dated Mar. 26, 2019, 8 pages.

(Continued)

*Primary Examiner* — Peter J Reddig
*Assistant Examiner* — Cheng Lu
(74) *Attorney, Agent, or Firm* — Goodwin Procter LLP

(57) ABSTRACT

The present invention provides PD-1 monoclonal antibodies, particularly human monoclonal antibodies of PD-1, which specifically bind to PD-1 with high affinity and comprise a heavy chain and a light chain. The present invention further provides nucleic acid sequence encoding the antibodies of the invention, cloning or expression vectors, host cells and methods for expressing or isolating the antibodies. Immunoconjugates, therapeutic compositions comprising the antibodies of the invention are also provided. The invention also provides methods for treating various cancers with anti-PD-1 antibodies.

18 Claims, 16 Drawing Sheets
Specification includes a Sequence Listing.

(56) References Cited

OTHER PUBLICATIONS

Agata et al., "Expression of the PD-1 Antigen on the Surface of Stimulated Mouse T and B Lymphocytes," International Immunology, vol. 8, No. 5, 1996, pp. 765-772.

Bennett et al., "Program Death-1 Engagement Upon TCR Activation Has Distinct Effects on Costimulation and Cytokine-Driven Proliferation: Attenuation of ICOS, IL-4, and IL-21, But Not CD28, IL-7, and IL-15 Responses," J Immunol, 2003; 170:711-718.

Blank et al., "Interaction of PD-L1 on Tumor Cells with PD-1 on Tumor-Specific T Cells as a Mechanism of Immune Evasion: Implications for Tumor Immunotherapy," Cancer Immunol Immunother (2005) 54 pp. 307-314.

Carter et al., "PD-1:PD-L Inhibitory Pathway Affects Both CD4+ and CD8+ T Cells and is Overcome by IL-2," Eur. J. Immunol. 2002, 32 pp. 634-643.

Dong et al., "B7-H1 Pathway and its Role in the Evasion of Tumor Immunity," J Mol Med (2003) 81, pp. 281-287.

Dong et al., "Tumor-Associated B7-H1 Promotes T-Cell Apoptosis: A Potential Mechanism of Immune Evasion," Nature Medicine, vol. 8, No. 8, Aug. 2002, pp. 793-799.

Freeman et al., "Engagement of the PD-1 Immunoinhibitory Receptor by a Novel B7 Family Member Leads to Negative Regulation of Lymphocyte Activation," J. Exp. Med., vol. 192, No. 7, Oct. 2, 2000, pp. 1027-1034.

Ishida et al., "Induced Expression of PD-1, a Novel Member of the Immunoglobulin Gene Superfamily, Upon Programmed Cell Death," The EMBO Journal, vol. 11, No. 11, 1992, pp. 3887-3895.

Konisha et al., "B7-H1 Expression on Non-Small Cell Lung Cancer Cells and Its Relationship with Tumor-Infiltrating Lymphocytes and Their PD-1 Expression," Clinical Cancer Research, vol. 10, Aug. 1, 2004, pp. 5094-5100.

Latchman et al., "PD-L2 is a Second Ligand for PD-1 and Inhibits T Cell Activation," Nature Immunology, Mar. 2001, vol. 2, No. 3, pp. 261-268.

Lin et al., "The PD-1/PD-L1 Complex Resembles the Antigen-Binding Fv Domains of Antibodies and T Cell Receptors," PNAS, Feb. 26, 2008, vol. 105, No. 8, pp. 3011-3016.

Nishimura et al., "Autoimmune Dilated Cardiomyopathy in PD-1 Receptor-Deficient Mice," Science, vol. 291, Jan. 12, 2001, pp. 319-322.

Nishimura et al., "Development of Lupus-Like Autoimmune Diseases by Disruption of the PD-1 Encoding an ITIM Motif-Carrying Immunoreceptor," Immunity, vol. 11, Aug. 1999, vol. 11, pp. 141-151.

Okazaki et al., "New Regulatory Co-Receptors: Inducible Co-Stimulator and PD-1," Current Opinion in Immunology 2002, 14, pp. 779-782.

Okazaki et al., "PD-1 and PD-1 Ligands: From Discovery to Clinical Application," International Immunology, vol. 19, No. 7, 2007, pp. 813-824.

Okazaki et al., "PD-1 Immunoreceptor Inhibits B Cell Receptor-Mediated Signaling by Recruiting SRC Homology 2-Domain-Containing Tyrosine Phosphatase 2 to Phosphotyrosine," PNAS, Nov. 20, 2001, vol. 98, No. 24, pp. 13866-13871.

Prokunina et al., "The Genetic Basis of Systemic Lupus Erythematosus—Knowledge of Today and Thoughts of Tomorrow," Human Molecular Genetics, vol. 13, Issue Suppl 1, Apr. 1, 2004, pp. R143-R148.

Salama et al., "Critical Role of the Programmed Death-1 (PD-1) Pathway in Regulation of Experimental Autoimmune Encephalomyelitis," J Exp Med (2003) 198 (1): 71-78.

* cited by examiner

A

B

A

B

C

A

B

C

A

B

A

B

C

A

B

A

B

MONOCLONAL ANTIBODIES TO PROGRAMMED DEATH 1 (PD-1)

This application is a U.S. National Stage entry of PCT Application No. PCT/CN2016/099576, filed Sep. 21, 2016, the contents of which are incorporated herein by reference.

TECHNICAL FIELD

The present invention relates generally to antibodies of PD-1 and compositions thereof, and immunotherapy in the treatment of human disease using anti-PD-1 antibodies.

SEQUENCE LISTING

The instant application contains a Sequence Listing which has been submitted via EFS-Web and is hereby incorporated by reference in its entirety. Said ASCII copy, created on Mar. 15, 2019, is named EQR-003WOUS_SL.txt, and is 14,000 bytes in size.

BACKGROUND OF THE INVENTION

Increasing evidences from preclinical and clinical results have shown that targeting immune checkpoints is becoming the most promising approach to treat patients with cancers. The protein Programmed Death 1 (PD-1), an inhibitory member of the immunoglobulin super-family with homology to CD28, is expressed on activated B cells, T cells, and myeloid cells (Agata et al, supra; Okazaki et al (2002) *Curr. Opin. Immunol.* 14: 391779-82; Bennett et al. (2003) *J Immunol* 170:711-8) and has a critical role in regulating stimulatory and inhibitory signals in the immune system (Okazaki, Taku et al. 2007 *International Immunology* 19:813-824). PD-1 was discovered through screening for differential expression in apoptotic cells (Ishida et al (1992) *EMBO J* 11:3887-95).

The PD-1 is a type I transmembrane protein that is part of the Ig gene superfamily (Agata et al. (1996) *bit Immunol* 8: 765-72) and the structure of PD-1 consists of one immunoglobulin variable-like extracellular domain and a cytoplasmic domain containing an immunoreceptor tyrosine-based inhibitory motif (ITIM) and an immunoreceptor tyrosine-based switch motif (ITSM). Although structurally similar to CTLA-4, PD-1 lacks the MYPPPY motif that is critical for B7-1 and B7-2 binding. PD-1 has two known ligands, PD-L1 (B7-H1, CD274) and PD-L2 (B7-DC, CD273), which are cell surface expressed members of the B7 family (Freeman et al (2000) *J Exp Med* 192: 1027-34; Latchman et al (2001) *Nat Immunol* 2:261-8; Carter et al (2002) *Eur J Immunol* 32:634-43). Both PD-L1 and PD-L2 are B7 homologs that bind to PD-1, but do not bind to other CD28 family members.

PD-1, as one of the immune-checkpoint proteins, is an inhibitory member of the CD28 family expressed on activated B cells, T cells, and myeloid cells (Agata et al, supra; Okazaki et al. (2002) *Curr Opin Immunol* 14: 391779-82; Bennett et al. (2003) *J Immunol* 170:711-8) plays a major role in limiting the activity of T cells that provide a major immune resistance mechanism by which tumor cells escaped immune surveillance. PD-1 induces a state of anergy or unresponsiveness in T cells, resulting in the cells being unable to produce optimal levels of effector cytokines. PD-1 may also induce apoptosis in T cells via its ability to inhibit survival signals. PD-1 deficient animals develop various autoimmune phenotypes, including autoimmune cardiomyopathy and a lupus-like syndrome with arthritis and nephritis (Nishimura et al. (1999) *Immunity* 11:141-51; Nishimura et al. (2001) *Science* 291:319-22). Additionally, PD-1 has been found to play a role in autoimmune encephalomyelitis, systemic lupus erythematosus, graft-versus-host disease (GVHD), type I diabetes, and rheumatoid arthritis (Salama et al. (2003) *J Exp Med* 198:71-78: Prokunina and Alarcon-Riquelme (2004) *Hum Mol Genet* 13:R143; Nielsen et al. (2004) *Lupus* 11:510). In a murine B cell tumor line, the ITSM of PD-1 was shown to be essential to block BCR-mediated $Ca^{2+}$-flux and tyrosine phosphorylation of downstream effector molecules (Okazaki et al. (2001) *PNAS* 98: 13866-71).

The interaction of PD-1 expressed on activated T cells, and PD-L1 expressed on tumor cells negatively regulates immune response and damps anti-tumor immunity. PD-L1 is abundant in a variety of human cancers (Dong et al (2002) *Nat. Med* 8:787-9). Expression of PD-L1 on tumors is correlated with reduced survival in esophageal, pancreatic and other types of cancers, highlighting this pathway as a new promising target for tumor immunotherapy. Several groups have shown that the PD-1-PD-L interaction exacerbates disease, resulting in a decrease in tumor infiltrating lymphocytes, a decrease in T-cell receptor mediated proliferation, and immune evasion by the cancerous cells (Dong et al. (2003) *J. Mol. Med.* 81:281-7; Blank et al. (2005) *Cancer Immunol. Immunother* 54:307-314; Konishi et al. (2004) *Clin. Cancer Res.* 10:5094-100). Immune suppression can be reversed by inhibiting the local interaction of PD-1 with PD-L1, and the effect is additive when the interaction of PD-1 with PD-L2 is blocked as well.

Multiple agents targeting PD-1 pathway have been developed by several pharmaceutical companies, such as Bristol-Myers Squibb (BMS), Merck, Roche and GlaxoSmithKline (GSK). Data from clinical trials demonstrated early evidence of durable clinical activity and an encouraging safety profile in patients with various tumor types. Nivolumab, an anti-PD-1 drug developed by BMS, is being put at center stage of the next-generation field. Now in 6 late-stage studies, the treatment spurred tumor shrinkage in three out of five cancer groups studied, including 18% of lung cancer patients (n=72), close to one third of melanoma patients (n=98) and 27% of patients with kidney cancer (n=33). Developed by Merck, Pembrolizumab is a humanized monoclonal IgG4 antibody that acts against PD-1, which grabbed the FDA's new breakthrough designation after impressive IB data came through for skin cancer. The results from a phase IB study have shown an objective anti-tumor response in 51% of the cancer patients (n=85), and a complete response in 9% of the patients. Roche's experimental MPDL3280A (Atezolizumab) demonstrated an ability to shrink tumors in 29 of 140 (21%) advanced cancer patients with various tumor sizes.

There are some spaces for improvement for antibody against PD-1 as a therapeutic agent. Most of monoclonal antibodies against PD-1 currently tested in clinical trials are only against to human PD-1 which limits preclinical in vivo assay and diminished efficacy owing to the immunogenicity of the mouse-derived protein sequences. Humanized antibody with cross-reactivity to mouse PD-1 overcome these shortages and showed more tolerability and higher efficiency in vivo. Thus there is still a need for novel anti-PD-1 antibody.

DISCLOSURE OF THE INVENTION

The present invention provides isolated antibodies, in particular monoclonal antibodies or human monoclonal antibodies.

In one aspect, the present invention provides an antibody or antigen binding fragment thereof that binds to an epitope of PD-1 comprising amino acids at positions 128, 129, 130, 131 and 132 and at least one of amino acids at positions 35, 64, 82, 83 of SEQ ID NO: 24.

The present invention also provides an antibody or antigen binding fragment thereof that binds to an epitope of human and murine PD-1, wherein the epitope comprises amino acids at positions 128, 129, 130, 131 and 132 of SEQ ID NO: 24.

The aforesaid antibody or the antigen binding fragment thereof, wherein the murine PD-1 is mouse or rat PD-1.

The aforesaid antibody or antigen binding fragment thereof, wherein the antibody
- a) binds to human PD-1 with a $K_D$ of 2.15E-10 M or less; and
- b) binds to mouse PD-1 with a $K_D$ of 1.67E-08 M or less.

The aforesaid antibody, wherein the antibody
- a) binds to human PD-1 with a $K_D$ of 2.15E-10 M or less; and
- b) binds to mouse PD-1 with a $K_D$ of 1.67E-08 M or less, and wherein the antibody exhibits at least one of the following properties:
- a) binds to human PD-1 with a $K_D$ of between 4.32E-10 M and 2.15E-10 M and to mouse PD-1 with a $K_D$ of between 5.39E-8 M and 1.67E-8 M;
- b) does not substantially bind to human CD28, CTLA-4;
- c) increases T-cell proliferation;
- d) increases interferon-gamma production; or
- e) increases interleukin-2 secretion.

The present invention provides an antibody or an antigen binding fragment thereof, comprising an amino acid sequence that is at least 70%, 80%, 90% or 95% homologous to a sequence selected from a group consisting of SEQ ID NOs: 1, 2, 3, 4, 5, 6, 7, 8 and 9, wherein the antibody specifically binds to PD-1.

The present invention provides an antibody or an antigen binding fragment thereof, comprising an amino acid sequence selected from a group consisting of SEQ ID NOs: 1, 2, 3, 4, 5, 6, 7, 8 and 9, wherein the antibody specifically binds to PD-1.

The present invention provides an antibody, or an antigen-binding fragment thereof, comprising:
- a) a variable region of a heavy chain having an amino acid sequence that is at least 70%, 80%, 90% or 95% homologous to a sequence selected from a group consisting of SEQ ID NOs: 1 and 2; and
- b) a variable region of a light chain having an amino acid sequence that is at least 70%, 80%, 90% or 95% homologous to a sequence selected from a group consisting of SEQ ID NOs: 3, 4, 5, 6, 7, 8 and 9, wherein the antibody specifically binds to PD-1.

The present invention provides an antibody or an antigen binding fragment thereof, comprising:
- a) a variable region of a heavy chain having an amino acid sequence selected from the group consisting of SEQ ID NOs: 1 and 2; and
- b) a variable region of a light chain having an amino acid sequence selected from the group consisting of SEQ ID NOs: 3, 4, 5, 6, 7, 8 and 9, wherein the antibody specifically binds to PD-1.

In various embodiments, the antibody comprises:
- a) a variable region of a heavy chain having an amino acid sequence selected from the group consisting of SEQ ID NO: 1; and
- b) a variable region of a light chain having an amino acid sequence selected from the group consisting of SEQ ID NO: 3, wherein the antibody specifically binds to PD-1;
or the antibody comprises:
- a) a variable region of a heavy chain having an amino acid sequence selected from the group consisting of SEQ ID NO: 2; and
- b) a variable region of a light chain having an amino acid sequence selected from the group consisting of SEQ ID NO: 3, wherein the antibody specifically binds to PD-1;
or the antibody comprises:
- a) a variable region of a heavy chain having an amino acid sequence selected from the group consisting of SEQ ID NO: 2; and
- b) a variable region of a light chain having an amino acid sequence selected from the group consisting of SEQ ID NO: 4, wherein the antibody specifically binds to PD-1;
or the antibody comprises:
- a) a variable region of a heavy chain having an amino acid sequence selected from the group consisting of SEQ ID NO: 2; and
- b) a variable region of a light chain having an amino acid sequence selected from the group consisting of SEQ ID NO: 5, wherein the antibody specifically binds to PD-1;
or the antibody comprises:
- a) a variable region of a heavy chain having an amino acid sequence selected from the group consisting of SEQ ID NO: 1; and
- b) a variable region of a light chain having an amino acid sequence selected from the group consisting of SEQ ID NO: 6, wherein the antibody specifically binds to PD-1;
or the antibody comprises:
- a) a variable region of a heavy chain having an amino acid sequence selected from the group consisting of SEQ ID NO: 1; and
- b) a variable region of a light chain having an amino acid sequence selected from the group consisting of SEQ ID NO: 5, wherein the antibody specifically binds to PD-1;
or the antibody comprises:
- a) a variable region of a heavy chain having an amino acid sequence selected from the group consisting of SEQ ID NO: 2; and
- b) a variable region of a light chain having an amino acid sequence selected from the group consisting of SEQ ID NO: 6, wherein the antibody specifically binds to PD-1;
or the antibody comprises:
- a) a variable region of a heavy chain having an amino acid sequence selected from the group consisting of SEQ ID NO: 2; and
- b) a variable region of a light chain having an amino acid sequence selected from the group consisting of SEQ ID NO: 7, wherein the antibody specifically binds to PD-1;
or the antibody comprises:
- a) a variable region of a heavy chain having an amino acid sequence selected from the group consisting of SEQ ID NO: 1; and b) a variable region of a light chain having an amino acid sequence selected from the group consisting of SEQ ID NO: 8,
wherein the antibody specifically binds to PD-1;
or the antibody comprises:
a) a variable region of a heavy chain having an amino acid sequence selected from the group consisting of SEQ ID NO: 2; and
b) a variable region of a light chain having an amino acid sequence selected from the group consisting of SEQ ID NO: 9,
wherein the antibody specifically binds to PD-1.

The sequence of the said antibody is shown in Table 1 and Sequence Listing.

TABLE 1

Sequence of the antibody

| Clone ID | | SEQ ID NO | Amino acid sequence |
|---|---|---|---|
| 1H6 | Heavy chain | 1 | QVQLVQSGAEVKKPGSSVKVSCKASGFTFTTYYISW VRQAPGQGLEYLGYINMGSGGTNYNEKFKGRVTITA DKSTSTAYMELSSLRSEDTAVYYCAILGYFDYWGQG TMVTVSS |
| | Light chain | 3 | DVVMTQSPLSLPVTLGQPASISCRSSQSLLDSDGGTY LYWFQQRPGQSPRRLIYLVSTLGSGVPDRFSGSGSGT DFTLKISRVEAEDVGVYYCMQLTHWPYTFGQGTKLE IK |
| 2E5 | Heavy chain | 2 | QVQLVQSGAEVKKPGSSVKVSCKASGFTFTTYYISW VRQAPGQGLEYLGYINMGSGGTNYNEKFKGRVTITA DKSTSTAYMELSSLRSEDTAVYYCAIIGYFDYWGQGT MVTVSS |
| | Light chain | 3 | DVVMTQSPLSLPVTLGQPASISCRSSQSLLDSDGGTY LYWFQQRPGQSPRRLIYLVSTLGSGVPDRFSGSGSGT DFTLKISRVEAEDVGVYYCMQLTHWPYTFGQGTKLE IK |
| 2G4 | Heavy chain | 2 | QVQLVQSGAEVKKPGSSVKVSCKASGFTFTTYYISW VRQAPGQGLEYLGYINMGSGGTNYNEKFKGRVTITA DKSTSTAYMELSSLRSEDTAVYYCAIIGYFDYWGQGT MVTVSS |
| | Light chain | 4 | DVVMTQSPLSLPVTLGQPASISCRSSQSLLDSDGSTYL YWFQQRPGQSPRRLIYLVSTLGSGVPDRFSGSGSGTD FTLKISRVEAEDVGVYYCMQLTHWPYTFGQGTKLEI K |
| 2C2 | Heavy chain | 2 | QVQLVQSGAEVKKPGSSVKVSCKASGFTFTTYYISW VRQAPGQGLEYLGYINMGSGGTNYNEKFKGRVTITA DKSTSTAYMELSSLRSEDTAVYYCAIIGYFDYWGQGT MVTVSS |
| | Light chain | 5 | DVVMTQSPLSLPVTLGQPASISCRSSQSLLDSDGATYL YWFQQRPGQSPRRLIYLVSTLGSGVPDRFSGSGSGTD FTLKISRVEAEDVGVYYCMQLTHWPYTFGQGTKLEI K |
| A6W | Heavy chain | 1 | QVQLVQSGAEVKKPGSSVKVSCKASGFTFTTYYISW VRQAPGQGLEYLGYINMGSGGTNYNEKFKGRVTITA DKSTSTAYMELSSLRSEDTAVYYCAILGYFDYWGQG TMVTVSS |
| | Light chain | 6 | DVVMTQSPLSLPVTLGQPASISCRSSQSLLDSDGNTY LYWFQQRPGQSPRRLIYLVSTLGSGVPDRFSGSGSGT DFTLKISRVEAEDVGVYYCMQLTHWPYTFGQGTKLE IK |
| 1G10 | Heavy chain | 1 | QVQLVQSGAEVKKPGSSVKVSCKASGFTFTTYYISW VRQAPGQGLEYLGYINMGSGGTNYNEKFKGRVTITA DKSTSTAYMELSSLRSEDTAVYYCAILGYFDYWGQG TMVTVSS |
| | Light chain | 5 | DVVMTQSPLSLPVTLGQPASISCRSSQSLLDSDGATYL YWFQQRPGQSPRRLIYLVSTLGSGVPDRFSGSGSGTD FTLKISRVEAEDVGVYYCMQLTHWPYTFGQGTKLEI K |
| 2B1 | Heavy chain | 2 | QVQLVQSGAEVKKPGSSVKVSCKASGFTFTTYYISW VRQAPGQGLEYLGYINMGSGGTNYNEKFKGRVTITA DKSTSTAYMELSSLRSEDTAVYYCAIIGYFDYWGQGT MVTVSS |
| | Light chain | 6 | DVVMTQSPLSLPVTLGQPASISCRSSQSLLDSDGNTY LYWFQQRPGQSPRRLIYLVSTLGSGVPDRFSGSGSGT DFTLKISRVEAEDVGVYYCMQLTHWPYTFGQGTKLE IK |

TABLE 1-continued

Sequence of the antibody

| Clone ID | | SEQ ID NO | Amino acid sequence |
|---|---|---|---|
| L1I | Heavy chain | 2 | QVQLVQSGAEVKKPGSSVKVSCKASGFTFTTYYISW VRQAPGQGLEYLGYINMGSGGTNYNEKFKGRVTITA DKSTSTAYMELSSLRSEDTAVYYCAIIGYFDYWGQGT MVTVSS |
| | Light chain | 7 | DVVMTQSPLSLPVTLGQPASISCRSSQSLLDSDGNTY LYWFQQRPGQSPRRLIYLVSTLGSGVPDRFSGSGSGT DFTLKISRVEAEDVGVYYCMQLTHAPYTFGQGTKLE IK |
| 5C4 | Heavy chain | 1 | QVQLVQSGAEVKKPGSSVKVSCKASGFTFTTYYISW VRQAPGQGLEYLGYINMGSGGTNYNEKFKGRVTITA DKSTSTAYMELSSLRSEDTAVYYCAILGYFDYWGQG TMVTVSS |
| | Light chain | 8 | DVVMTQSPLSLPVTLGQPASISCRSSQSLLDSDGQTY LYWFQQRPGQSPRRLIYLVSTLGSGVPDRFSGSGSGT DFTLKISRVEAEDVGVYYCMQLTHEPYTFGQGTKLEI K |
| 8C10 | Heavy chain | 2 | QVQLVQSGAEVKKPGSSVKVSCKASGFTFTTYYISW VRQAPGQGLEYLGYINMGSGGTNYNEKFKGRVTITA DKSTSTAYMELSSLRSEDTAVYYCAIIGYFDYWGQGT MVTVSS |
| | Light chain | 9 | DVVMTQSPLSLPVTLGQPASISCRSSQSLLDSDGQTY LYWFQQRPGQSPRRLIYLVSTLGSGVPDRFSGSGSGT DFTLKISRVEAEDVGVYYCMQLTHENYTFGQGTKLE IK |

In another aspect, the invention provides an antibody or an antigen binding fragment thereof, comprising a complementarity-determining region (CDR) having an amino acid sequence selected from the group consisting of SEQ ID NOs: 10-23, wherein the antibody specifically binds to PD-1.

In another aspect, the invention provides an antibody, or antigen-binding fragment thereof, comprising: a heavy chain variable region comprising CDR1, CDR2, and CDR3 sequences; and a light chain variable region comprising CDR1, CDR2, and CDR3 sequences, wherein the heavy chain variable region CDR3 sequence comprises a sequence selected from a group consisting of SEQ ID NOs: 12 and 13, and conservative modifications thereof, wherein the antibody specifically binds to PD-1.

Preferably, wherein the light chain variable region CDR3 sequence of the aforesaid antibody comprises an amino acid sequence selected from a group consisting of SEQ ID NOs: 20, 21, 22 and 23, and conservative modifications thereof.

Preferably, wherein the heavy chain variable region CDR2 sequence of the aforesaid antibody comprises an amino acid sequence selected from a group consisting of amino acid sequences of SEQ ID NO: 11, and conservative modifications thereof.

Preferably, wherein the light chain variable region CDR2 sequence of the aforesaid antibody comprises an amino acid sequence selected from a group consisting of amino acid sequences of SEQ ID NO: 19, and conservative modifications thereof.

Preferably, wherein the heavy chain variable region CDR1 sequence of the aforesaid antibody comprises an amino acid sequence selected from a group consisting of amino acid sequences of SEQ ID NO: 10, and conservative modifications thereof.

Preferably, the antibody of this invention, wherein light chain variable region CDR1 sequence of the aforesaid antibody comprises an amino acid sequence selected from a group consisting of amino acid sequences of SEQ ID NO: 14, 15, 16, 17 and 18, and conservative modifications thereof.

In more preferred embodiment, the invention provides an antibody, or an antigen-binding fragment thereof, wherein the antibody specifically binds to PD-1 and comprises: a heavy chain variable region that comprises CDR1, CDR2, and CDR3 sequences; and a light chain variable region that comprises CDR1, CDR2, and CDR3 sequences, wherein:

a) the heavy chain variable region CDR1 sequence comprises SEQ ID NO: 10, and CDR2 sequence comprises an amino acid sequence selected from the SEQ ID NO: 11, CDR3 sequence comprises an amino acid sequence selected from the group consisting of amino acid sequences of SEQ ID NOs: 12-13;

b) and the light chain variable region CDR1 sequence comprises an amino acid sequence selected from the group consisting of amino acid sequences of SEQ ID NOs: 14-18, CDR2 sequence comprises an amino acid sequence selected from the group consisting of amino acid sequences of SEQ ID NO: 19, CDR3 sequence comprises an amino acid sequence selected from the group consisting of amino acid sequences of SEQ ID NOs: 20-23.

A preferred antibody comprises:
a) a heavy chain variable region CDR1 comprising SEQ ID NO: 10;
b) a heavy chain variable region CDR2 comprising SEQ ID NO: 11;
c) a heavy chain variable region CDR3 comprising SEQ ID NO: 12;
d) a light chain variable region CDR1 comprising SEQ ID NOs: 14;
e) a light chain variable region CDR2 comprising SEQ ID NOs: 19;
f) a light chain variable region CDR3 comprising SEQ ID NOs: 20;

wherein the antibody specifically binds to PD-1.

Another preferred antibody comprises:
a) a heavy chain variable region CDR1 comprising SEQ ID NO: 10;
b) a heavy chain variable region CDR2 comprising SEQ ID NOs: 11;
c) a heavy chain variable region CDR3 comprising SEQ ID NOs: 13;
d) a light chain variable region CDR1 comprising SEQ ID NOs: 14;
e) a light chain variable region CDR2 comprising SEQ ID NO: 19;
f) a light chain variable region CDR3 comprising SEQ ID NO: 21;
wherein the antibody specifically binds to PD-1.
Another preferred antibody comprises:
a) a heavy chain variable region CDR1 comprising SEQ ID NO: 10;
b) a heavy chain variable region CDR2 comprising SEQ ID NO: 11;
c) a heavy chain variable region CDR3 comprising SEQ ID NO: 13;
d) a light chain variable region CDR1 comprising SEQ ID NO: 15;
e) a light chain variable region CDR2 comprising SEQ ID NO: 19;
f) a light chain variable region CDR3 comprising SEQ ID NO: 21;
wherein the antibody specifically binds to PD-1.
Another preferred antibody comprises:
a) a heavy chain variable region CDR1 comprising SEQ ID NO: 10;
b) a heavy chain variable region CDR2 comprising SEQ ID NO: 11;
c) a heavy chain variable region CDR3 comprising SEQ ID NO: 13;
d) a light chain variable region CDR1 comprising SEQ ID NO: 16;
e) a light chain variable region CDR2 comprising SEQ ID NO: 19;
f) a light chain variable region CDR3 comprising SEQ ID NO: 21;
wherein the antibody specifically binds to PD-1.
Another preferred antibody comprises:
a) a heavy chain variable region CDR1 comprising SEQ ID NO: 10;
b) a heavy chain variable region CDR2 comprising SEQ ID NO: 11;
c) a heavy chain variable region CDR3 comprising SEQ ID NO: 12;
d) a light chain variable region CDR1 comprising SEQ ID NO: 17;
e) a light chain variable region CDR2 comprising SEQ ID NO: 19;
f) a light chain variable region CDR3 comprising SEQ ID NO: 21;
wherein the antibody specifically binds to PD-1.
Another preferred antibody comprises:
a) a heavy chain variable region CDR1 comprising SEQ ID NO: 10;
b) a heavy chain variable region CDR2 comprising SEQ ID NO: 11;
c) a heavy chain variable region CDR3 comprising SEQ ID NO: 12;
d) a light chain variable region CDR1 comprising SEQ ID NO: 16;
e) a light chain variable region CDR2 comprising SEQ ID NO: 19;
f) a light chain variable region CDR3 comprising SEQ ID NO: 21;
wherein the antibody specifically binds to PD-1.
Another preferred antibody comprises:
a) a heavy chain variable region CDR1 comprising SEQ ID NO: 10;
b) a heavy chain variable region CDR2 comprising SEQ ID NO: 11;
c) a heavy chain variable region CDR3 comprising SEQ ID NO: 13;
d) a light chain variable region CDR1 comprising SEQ ID NO: 17;
e) a light chain variable region CDR2 comprising SEQ ID NO: 19;
f) a light chain variable region CDR3 comprising SEQ ID NO: 21;
wherein the antibody specifically binds to PD-1.
Another preferred antibody comprises:
a) a heavy chain variable region CDR1 comprising SEQ ID NO: 10;
b) a heavy chain variable region CDR2 comprising SEQ ID NO: 11;
c) a heavy chain variable region CDR3 comprising SEQ ID NO: 13;
d) a light chain variable region CDR1 comprising SEQ ID NO: 17;
e) a light chain variable region CDR2 comprising SEQ ID NO: 19;
f) a light chain variable region CDR3 comprising SEQ ID NO: 22;
wherein the antibody specifically binds to PD-1.
Another preferred antibody comprises:
a) a heavy chain variable region CDR1 comprising SEQ ID NO: 10;
b) a heavy chain variable region CDR2 comprising SEQ ID NO: 11;
c) a heavy chain variable region CDR3 comprising SEQ ID NO: 12;
d) a light chain variable region CDR1 comprising SEQ ID NO: 18;
e) a light chain variable region CDR2 comprising SEQ ID NO: 19;
f) a light chain variable region CDR3 comprising SEQ ID NO: 23;
wherein the antibody specifically binds to PD-1.
Another preferred antibody comprises:
a) a heavy chain variable region CDR1 comprising SEQ ID NO: 10;
b) a heavy chain variable region CDR2 comprising SEQ ID NO: 11;
c) a heavy chain variable region CDR3 comprising SEQ ID NO: 12;
d) a light chain variable region CDR1 comprising SEQ ID NO: 18;
e) a light chain variable region CDR2 comprising SEQ ID NO: 19;
f) a light chain variable region CDR3 comprising SEQ ID NO: 20;
wherein the antibody specifically binds to PD-1.
The CDR sequence of the said antibody is shown in Table 2 and Sequence Listing.

TABLE 2

Sequence of the antibody

| Clone ID. | | SEQ ID NO | CDR1 | SEQ ID NO | CDR2 | SEQ ID NO | CDR3 |
|---|---|---|---|---|---|---|---|
| 1H6 | Heavy chain | 10 | TYYIS | 11 | YINMGSGGTNYNEKFKG | 12 | LGYFDY |
| | Light chain | 14 | RSSQSLLDSDGGTYLY | 19 | LVSTLGS | 20 | MQLTHENYT |
| 2E5 | Heavy chain | 10 | TYYIS | 11 | YINMGSGGTNYNEKFKG | 13 | IGYFDY |
| | Light chain | 14 | RSSQSLLDSDGGTYLY | 19 | LVSTLGS | 21 | MQLTHWPYT |
| 2G4 | Heavy chain | 10 | TYYIS | 11 | YINMGSGGTNYNEKFKG | 13 | IGYFDY |
| | Light chain | 15 | RSSQSLLDSDGSTYLY | 19 | LVSTLGS | 21 | MQLTHWPYT |
| 2C2 | Heavy chain | 10 | TYYIS | 11 | YINMGSGGTNYNEKFKG | 13 | IGYFDY |
| | Light chain | 16 | RSSQSLLDSDGATYLY | 19 | LVSTLGS | 21 | MQLTHWPYT |
| A6W | Heavy chain | 10 | TYYIS | 11 | YINMGSGGTNYNEKFKG | 12 | LGYFDY |
| | Light chain | 17 | RSSQSLLDSDGNTYLY | 19 | LVSTLGS | 21 | MQLTHWPYT |
| 1G10 | Heavy chain | 10 | TYYIS | 11 | YINMGSGGTNYNEKFKG | 12 | LGYFDY |
| | Light chain | 16 | RSSQSLLDSDGATYLY | 19 | LVSTLGS | 21 | MQLTHWPYT |
| 2B1 | Heavy chain | 10 | TYYIS | 11 | YINMGSGGTNYNEKFKG | 13 | IGYFDY |
| | Light chain | 17 | RSSQSLLDSDGNTYLY | 19 | LVSTLGS | 21 | MQLTHWPYT |
| L1I | Heavy chain | 10 | TYYIS | 11 | YINMGSGGTNYNEKFKG | 13 | IGYFDY |
| | Light chain | 17 | RSSQSLLDSDGNTYLY | 19 | LVSTLGS | 22 | MQLTHAPYT |
| 5C4 | Heavy chain | 10 | TYYIS | 11 | YINMGSGGTNYNEKFKG | 12 | LGYFDY |
| | Light chain | 18 | RSSQSLLDSDGQTYLY | 19 | LVSTLGS | 23 | MQLTHEPYT |
| 8C10 | Heavy chain | 10 | TYYIS | 11 | YINMGSGGTNYNEKFKG | 12 | LGYFDY |
| | Light chain | 18 | RSSQSLLDSDGQTYLY | 19 | LVSTLGS | 20 | MQLTHENYT |

The antibodies of the invention can be chimeric or humanized or human antibody.

The antibodies of the invention can exhibit at least one of the following properties:
  a) binds to human PD-1 with a $K_D$ of 2.15E-10 M or less and to mouse PD-1 with a $K_D$ of 1.67E-08 M or less;
  b) does not substantially bind to human CD28, CTLA-4;
  c) increases T-cell proliferation;
  d) increases interferon-gamma production; or
  e) increases interleukin-2 secretion.

In a further aspect, the invention provides a nucleic acid molecule encoding the antibody, or antigen binding fragment thereof.

The invention provides a cloning or expression vector comprising the nucleic acid molecule encoding the antibody, or antigen binding fragment thereof.

The invention also provides a host cell comprising one or more cloning or expression vectors.

In yet another aspect, the invention provides a process, comprising culturing the host cell of the invention and isolating the antibody, wherein the antibody is prepared through immunization in SD rat with human PD-1 extracellular domain and mouse PD-1 extracellular domain.

The invention provides a transgenic mouse comprising human immunoglobulin heavy and light chain transgenes, wherein the mouse expresses the antibody of this invention.

The invention provides hybridoma prepared from the mouse of this invention, wherein the hybridoma produces said antibody.

In a further aspect, the invention provides pharmaceutical composition comprising the antibody, or the antigen binding fragment of said antibody in the invention, and one or more of a pharmaceutically acceptable excipient, diluent or carrier.

The invention provides an immunoconjugate comprising the said antibody, or antigen-binding fragment thereof in this invention, linked to a therapeutic agent.

Wherein, the invention provides a pharmaceutical composition comprising the said immunoconjugate and a pharmaceutically acceptable excipient, diluent or carrier.

The invention also provides a method for preparing an anti-PD-1 antibody or an antigen-binding fragment thereof comprising:

(a) providing: (i) a heavy chain variable region antibody sequence comprising a CDR1 sequence that is selected from a group consisting of SEQ ID NO: 10, a CDR2 sequence that is selected from a group consisting of SEQ ID NO: 11; and a CDR3 sequence that is selected from the group consisting of SEQ ID NOs: 12 and 13; and/or (ii) a light chain variable region antibody sequence comprising a CDR1 sequence that is selected from the group consisting of SEQ ID NOs: 14, 15, 16, 17 and 18, a CDR2 sequence that is selected from the group consisting of SEQ ID NO: 19, and a CDR3 sequence that is selected from the group consisting of SEQ ID NOs: 20, 21, 22 and 23; and (b) expressing the altered antibody sequence as a protein.

The invention also provides a method of modulating an immune response in a subject comprising administering to the subject the antibody, or antigen binding fragment of any one of said antibodies in this invention.

The invention also provides the use of said antibody in the manufacture of a medicament for the treatment or prophylaxis of an immune disorder or cancer.

The invention also provides a method of inhibiting growth of tumor cells in a subject, comprising administering to the subject a therapeutically effective amount of the said antibody, or the said antigen-binding fragment to inhibit growth of the tumor cells.

Wherein, the invention provides the method, wherein the tumor cells are of a cancer selected from a group consisting of melanoma, renal cancer, prostate cancer, breast cancer, colon cancer, lung cancer, bone cancer, pancreatic cancer, skin cancer, cancer of the head or neck, cutaneous or intraocular malignant melanoma, uterine cancer, ovarian cancer, and rectal cancer.

Wherein, the invention provides the method, wherein the antibody is a chimeric antibody or humanized antibody.

The Features and Advantages of this Invention

The inventors have generated a humanized antibody against PD-1 utilizing the proprietary hybridoma technology. The antibodies reported in this invention have high binding affinity, specifically binding to both human and mouse PD-1 protein without cross-family reactions; and potent modulating immune responses, including enhancing T cell proliferation and increasing cytokine IFN-γ and interleukin-2 production.

New anti-PD-1 antibodies binding to mouse PD-1 are derived from immuned rats, which overcomes the disadvantage that is anti-PD-1 antibodies can not be used in pre-clinical mouse model; and the humanized level is close to 100% after sequence humanization, greatly reducing the adverse effects of drugs used in the human body.

BRIEF DESCRIPTION OF THE DRAWINGS

FIG. 1A shows binding to human PD-1. FIG. 1B shows binding to mouse PD-1.

FIG. 3A shows binding to human PD-1 transfected CHO-S cells. FIG. 3B shows binding to mouse PD-1 transfected 293F cells. FIG. 3C shows binding to activated cynomolgus PBMC. Note: the isotype was human IgG4 kappa. The same below.

FIG. 4A shows binding to human PD-1. FIG. 4B shows binding to mouse PD-1.

FIG. 4C shows binding to cynomolgus PD-1.

FIG. 8A shows binning against WBP305BMK1 (U.S. Pat. No. 9,084,776). FIG. 8B shows binning against Keytruda (U.S. Pat. No. 8,168,757).

FIG. 12A shows anti-PD-1 antibodies increase IL-2 secretion in a dose-dependent manner. FIG. 12B shows anti-PD-1 antibodies increase IFN-γ secretion in a dose-dependent manner. FIG. 12C shows anti-PD-1 antibodies increase CD4+ T cells proliferation in a dose-dependent manner.

FIG. 13A shows anti-PD-1 antibodies increase IL-2 secretion in a dose-dependent manner. FIG. 13B shows anti-PD-1 antibodies increase IFN-γ secretion in a dose-dependent manner. FIG. 13C shows anti-PD-1 antibodies increase CD4+ T cells proliferation in a dose-dependent manner.

FIG. 14A shows anti-PD-1 antibodies increase IFN-γ secretion in a dose-dependent manner. FIG. 14B shows anti-PD-1 antibodies increase CD4+ T cells proliferation in a dose-dependent manner.

FIG. 15A shows anti-PD-1 antibodies can restore the IFN-γ secretion. FIG. 15B shows anti-PD-1 antibodies can restore the T-cell proliferation.

DETAILED DESCRIPTION

Figure 1:
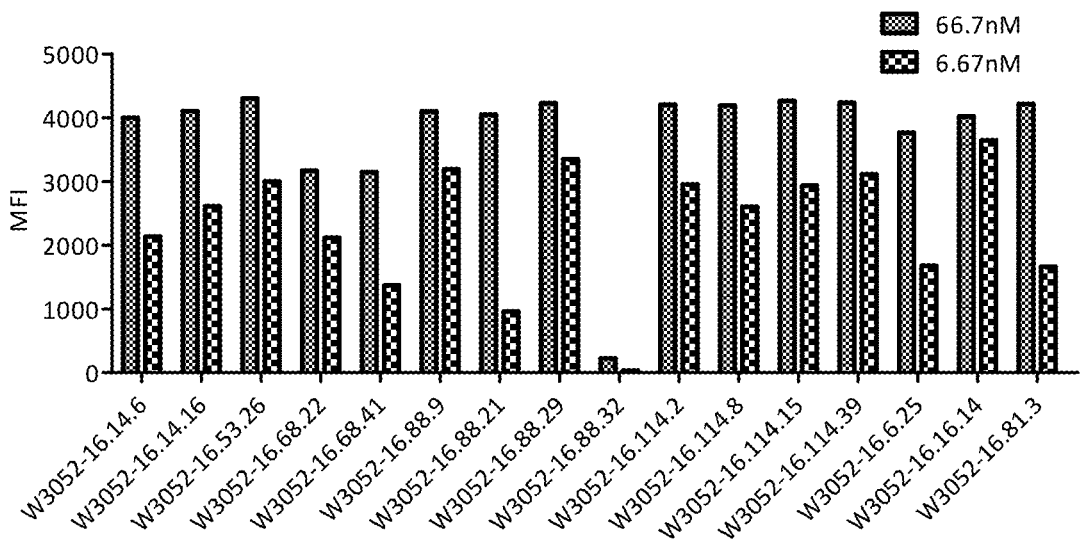
FIG. 1 shows graphs of hybridoma antibodies binding to cell surface human and mouse PD-1.
Figure 1:
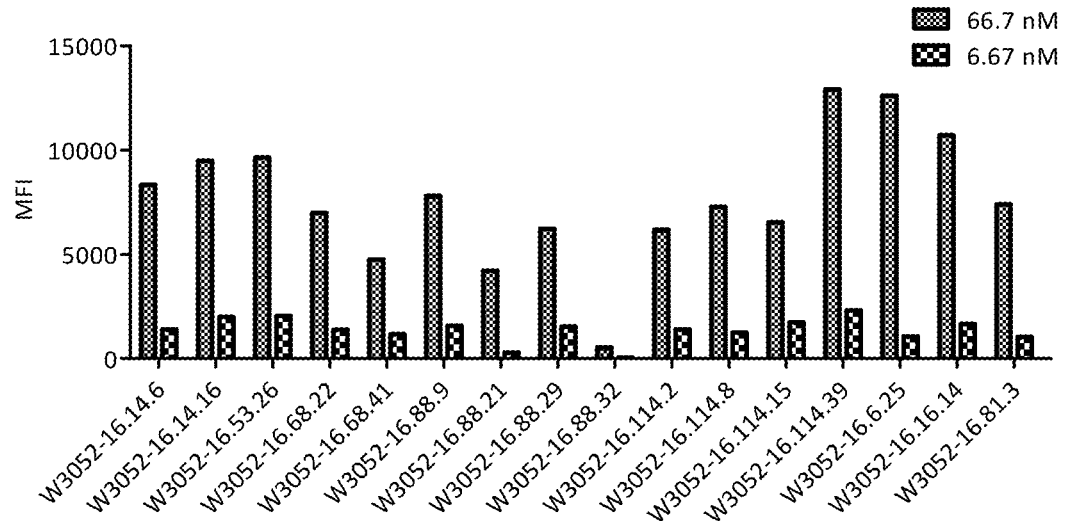

In order that the present invention may be more readily understood, certain terms are first defined. Additional definitions are set forth throughout the detailed description.

The terms "Programmed Death 1", "Programmed Cell Death 1", "Protein PD-1", "PD-1", "PD1", "PDCD1", "hPD-1" and "hPD-F" are used interchangeably, and include variants, isoforms, species homologs of human PD-1, and analogs having at least one common epitope with PD-1.

The term "antibody" as referred to herein includes whole antibodies and any antigen-binding fragment (i.e., "antigen-binding portion") or single chains thereof. An "antibody" refers to a protein comprising at least two heavy (H) chains and two light (L) chains inter-connected by disulfide bonds, or an antigen-binding portion thereof. Each heavy chain is comprised of a heavy chain variable region (abbreviated herein as VH) and a heavy chain constant region. The heavy chain constant region is comprised of three domains, CH1, CH2 and CH3. Each light chain is comprised of a light chain variable region (abbreviated herein as VL) and a light chain constant region. The light chain constant region is comprised of one domain, CL. The VH and VL regions can be further subdivided into regions of hypervariability, termed complementarity determining regions (CDR), interspersed with regions that are more conserved, termed framework regions (FR). Each VH and VL is composed of three CDRs and four FRs, arranged from amino-terminus to carboxy-terminus in the following order: FR1, CDR1, FR2, CDR2, FR3, CDR3, FR4. The variable regions of the heavy and light chains contain a binding domain that interacts with an antigen.

The term "antibody," as used in this disclosure, refers to an immunoglobulin or a fragment or a derivative thereof, and encompasses any polypeptide comprising an antigen-binding site, regardless whether it is produced in vitro or in vivo. The term includes, but is not limited to, polyclonal, monoclonal, monospecific, polyspecific, non-specific, humanized, single-chain, chimeric, synthetic, recombinant, hybrid, mutated, and grafted antibodies. The term "antibody" also includes antibody fragments such as Fab, F(ab')2, Fv, scFv, Fd, dAb, and other antibody fragments that retain antigen-binding function, i.e., the ability to bind PD-1 specifically. Typically, such fragments would comprise an antigen-binding fragment.

The terms "antigen-binding fragment," "antigen-binding domain," and "binding fragment" refer to a part of an antibody molecule that comprises amino acids responsible for the specific binding between the antibody and the antigen. In instances, where an antigen is large, the antigen-binding fragment may only bind to a part of the antigen. A portion of the antigen molecule that is responsible for specific interactions with the antigen-binding fragment is referred to as "epitope" or "antigenic determinant."

An antigen-binding fragment typically comprises an antibody light chain variable region (VL) and an antibody heavy chain variable region (VH), however, it does not necessarily have to comprise both. For example, a so-called Fd antibody fragment consists only of a VH domain, but still retains some antigen-binding function of the intact antibody.

In line with the above the term "epitope" defines an antigenic determinant, which is specifically bound/identified by a binding fragment as defined above. The binding fragment may specifically bind to/interact with conformational or continuous epitopes, which are unique for the target structure, e.g. the human and murine PD-1. A conformational or discontinuous epitope is characterized for polypeptide antigens by the presence of two or more discrete amino acid residues which are separated in the primary sequence, but come together on the surface of the molecule when the polypeptide folds into the native protein/antigen. The two or more discrete amino acid residues contributing to the epitope are present on separate sections of one or more polypeptide chain(s). These residues come together on the surface of the molecule when the polypeptide chain(s) fold(s) into a three-dimensional structure to constitute the epitope. In contrast, a continuous or linear epitope consists of two or more discrete amino acid residues, which are present in a single linear segment of a polypeptide chain.

The term "binds to an epitope of PD-1" refers to the antibodies have specific binding for a particular epitope of PD-1, which may be defined by a linear amino acid sequence, or by a tertiary, i.e., three-dimensional, conformation on part of the PD-1 polypeptide. Binding means that the antibodies affinity for the portion of PD-1 is substantially greater than their affinity for other related polypeptides. The term "substantially greater affinity" means that there is a measurable increase in the affinity for the portion of PD-1 as compared with the affinity for other related polypeptides. Preferably, the affinity is at least 1.5-fold, 2-fold, 5-fold 10-fold, 100-fold, $10^3$-fold, $10^4$-fold, $10^5$-fold, $10^6$-fold or greater for the particular portion of PD-1 than for other proteins. Preferably, the binding affinity is determined by enzyme-linked immunoabsorbent assay (ELISA), or by fluorescence-activated cell sorting (FACS) analysis or surface Plasmon resonance (SPR). More preferably, the binding specificity is obtained by fluorescence-activated cell sorting (FACS) analysis.

The term "cross-reactivity" refers to binding of an antigen fragment described herein to the same target molecule in human and murine (mouse or rat). Thus, "cross-reactivity" is to be understood as an interspecies reactivity to the same molecule X expressed in different species, but not to a molecule other than X. Cross-species specificity of a monoclonal antibody recognizing e.g. human PD-1, to a murine (mouse or rat) PD-1, can be determined, for instance, by FACS analysis.

As used herein, the term "subject" includes any human or nonhuman animal. The term "nonhuman animal" includes all vertebrates, e.g., mammals and non-mammals, such as nonhuman primates, sheep, dogs, cats, horses, cows, chickens, amphibians, reptiles, etc. Except when noted, the terms "patient" or "subject" are used interchangeably.

The terms "treatment" and "therapeutic method" refer to both therapeutic treatment and prophylactic/preventative measures. Those in need of treatment may include individuals already having a particular medical disorder as well as those who may ultimately acquire the disorder.

EXAMPLES

Example 1: Research Materials Preparation

1. Immunogen Generation

DNAs encoding the ECD or full length of PD-1 and PD-L1 were synthesized and inserted into the expression vector pcDNA3.3. Max-prep the plasmid DNAs and the inserted DNA sequences were verified by sequencing. Fusion proteins PD-1 ECD and PD-L1 ECD containing various tags, including human Fc, mouse Fc and His tags, were obtained by transfection of human PD-1 ECD gene into CHO-S or HEK293 cells. After 5 days, supernatants were harvested from the culture of transient transfected cells. The fusion proteins were purified and quantified for usage of immunization and screening.

2. Stable Cell Lines Establishment

In order to obtain tools for antibody screening and validation, we generated PD-1 and PD-L1 transfecting cell lines. Briefly, CHO-K1 or 293F cells were transfected with pcDNA3.3 expression vector containing full-length PD-1 or PD-L1 using Lipofectamine 2000 Transfection kit according to manufacturer's protocol. 48-72 hours post transfection; the transfected cells were cultured in medium containing Blasticidin or G418 to select the cells that had PD-1 or PD-L1 genes stably incorporated into their genomic DNAs. Meanwhile the cells were checked for interested genes PD-1 and PD-L1 expression. Once the expression verified, single clones of interested were picked by limited dilution and scaled up to large volumes. The established monoclonal cell lines were then maintained in medium containing lower dose of antibiotics Blasticidin or G418.

Example 2: Antibody Hybridoma Generation

1. Immunization

Female SD rats, at 6-8 weeks of age, were immunized with 10 μg/animal of human PD-1 ECD protein and 10 μg/animal of mouse PD-1 ECD protein in TiterMax by footpad injection for prime, and were boosted twice a week with human PD-1 ECD protein or mouse PD-1 ECD protein in Aluminium alternately. The serum antibody titers were measured by ELISA or FACS every two weeks.

2. Cell Fusion

When the serum antibody titer was sufficiently high, rats were given a final boost with both human and mouse PD-1 ECD protein in the equal volume of D-PBS (Dulbecco's Phosphate Buffered Saline) without adjuvant. The cell fusion was performed as follows: preparing myeloma cells SP2/0, myeloma cells were thawed the week before the fusion, and were split at 1:2 each day until the day before the fusion to keep in logarithmic growth. B lymphocytes isolated from lymph node of immunized SD rats were combined with myeloma cells (at 1:1 ratio). The cells were treated with Trypsin and the reaction was stopped by FBS. Cell mixture was then washed and re-suspended in ECF solution at $2 \times 10^6$ cells/ml for ECF. After electronic cell fusion (BTX2000), cell suspension from the fusion chamber was immediately transferred into a sterile tube containing more medium, and incubated for at least 24 hours in a 37° C. incubator. The cell suspension was then mixed and transferred into 96-well plates ($1 \times 10^4$ cells/well). The 96-well plates were cultured at 37° C., 5% $CO_2$, and were monitored periodically. When the clones were big enough (after 7-14 days), 100 μL of supernatant were transferred from the tissue culture plates to 96-well assay plates for antibody screening.

3. First, Second and Confirmation Screen of Hybridoma Supernatants

ELISA assay was used as first screen method to test the binding of hybridoma supernatants to human or mouse PD-1 protein. Briefly, plates (Nunc) were coated with human or mouse PD-1 ECD at 1 μg/ml overnight at 4° C. After blocking and washing, the hybridoma supernatants were loaded to the coated plates and incubated at room temperature for 1 h. The plates were then washed and subsequently incubated with secondary antibody goat anti rat IgG Fc HRP (Bethyl) for 1 h. After washing, TMB substrate was added and the reaction was stopped by 2M HCl. The absorbance at 450 nm was read using a microplate reader (Molecular Device).

In order to confirm the native binding of anti-PD-1 antibodies on conformational PD-1 molecules expressed on cell membrane, FACS analysis was performed using PD-1 transfected cell lines as second screening. CHO-S cells expressing human PD-1 or 293F cells expressing mouse PD-1 were transferred into 96-well U-bottom plates (Corning) at a density of $1 \times 10^5$ cells/well. The hybridoma supernatants were then added and incubated with the cells for 1 h at 4° C. After washing with 1×PBS/1% BSA, the secondary antibody goat anti rat FITC (Jackson ImmunoResearch Lab) was applied and incubated with cells at 4° C. in the dark for 1 h. The cells were then washed and resuspended in 1×PBS/1% BSA or fixed with 4% paraformaldehyde, and analyzed by flow cytometery (BD) and FlowJo software. Antibody binding to parental CHO-S or 293F cell line was used as negative control, respectively.

To select potential antagonistic hits, selected antibodies were tested for their ability to block the binding of the ligand PD-L1 to PD-1 transfected cells by FACS analysis. CHO-S cells expressing human PD-1 or 293F cells expressing mouse PD-1 were transferred into 96-well U-bottom plates (BD) at a density of $1 \times 10^5$ cells/well. Hybridoma supernatants were added and incubated with the cells at 4° C. for 1 h. After washing, mouse Fc fusion-human PD-L1 protein or mouse Fc fusion-mouse PD-L1 protein was added and incubated at 4° C. for 1 h. The secondary antibody goat anti mouse IgG Fc FITC antibody (no cross-reactivity to rat IgG Fc, Jackson ImmunoResearch Lab) was incubated with cells at 4° C. in the dark for 1 h. The cells were then washed and resuspended in 1×PBS/1% BSA or fixed with 4% paraformaldehyde, and analyzed by flow cytometery (BD) and FlowJo software.

FIG. 1 shows graphs of 16 hybridoma antibodies binding to cell surface human and mouse PD-1. FIG. 1A shows binding to human PD-1. FIG. 1B shows binding to mouse PD-1.

4. Hybridoma Subcloning

Once specific binding and blocking activity were verified through first and confirmation screening, the positive hybridoma cell lines were used for subcloning. Briefly, for each hybridoma cell line, cells were counted and diluted to give 5 cells, 1 cell or 0.5 cell per 200 μL cloning medium. The cell suspension was plated 200 μL/well into 96-well plates, one plate at 5 cells/well, one plate at 1 cell/well and four plates at 0.5 cell/well. Plates were cultured at 37° C., 5% CO$_2$, till they were ready to be screened by binding ELISA or FACS as described above. The ESN of selected single clones were collected, and the antibodies were purified for further characterization.

5. Subtypes Testing

50 μL of goat anti-rat IgG1, IgG2a, IgG2b, IgG2c, IgG or IgM antibodies (1 μg/mL) were coated in microtiter plates (Nunc) per well overnight. After blocking, 50 μL of hybridoma supernatant samples were added to each well, incubated for 2 hours at room temperature. Goat anti-rat IgG kappa or HRP labeled lambda light chain secondary antibody (Bethyl) is a detection antibody. Using TMB substrate for color, the reaction was then quenched with 2 M HCl. The value of absorbs light at 450 nm is read using a microplate reader (Molecular Device).

Table 3 shows the subtype results of 16 hybridoma antibodies. 7 antibodies are polyclonal antibodies, and 9 antibodies are IgG2a kappa subtype. Considering the needs of anti-PD-1 antibody to avoid the role of ADCC and CDC in vivo, the humanized antibody will be built as human IgG4 kappa subtype.

TABLE 3

Subtypes of the hybridoma antibodies

| Number | antibody | IgG1 | kappa IgG2a | IgG2b | IgM |
|---|---|---|---|---|---|
| 1 | W3052_r16.6.25 | − | − | + | weak |
| 2 | W3052_r16.14.6 | + | + | − | − |
| 3 | W3052_r16.14.16 | − | + | − | + |
| 4 | W3052_r16.16.14 | + | + | − | + |
| 5 | W3052_r16.53.26 | + | + | − | − |
| 6 | W3052_r16.68.22 | − | + | − | − |
| 7 | W3052_r16.68.41 | − | + | − | − |
| 8 | W3052_r16.81.3 | − | − | + | + |
| 9 | W3052_r16.88.9 | − | + | − | − |
| 10 | W3052_r16.88.21 | weak | + | − | − |
| 11 | W3052_r16.88.29 | − | weak | − | − |
| 12 | W3052_r16.88.32 | − | + | − | − |
| 13 | W3052_r16.114.2 | − | + | − | − |
| 14 | W3052_r16.114.8 | − | + | − | − |
| 15 | W3052_r16.114.15 | − | + | − | − |
| 16 | W3052_r16.114.39 | − | + | − | − |

Example 3: Antibody Hybridoma Cell Sequence and Humanized Antibody Molecules Construction and Affinity Maturation 1. Antibody Hybridoma Cell Sequence RNAs were isolated from monoclonal hybridoma cells with Trizol reagent. The VH and VL of PD-1 chimeric antibodies were amplified as follows: RNA is first reverse transcribed into cDNA using a reverse transcriptase as described here, Reaction System (20 μL)

| | |
|---|---|
| 10 × RT Buffer | 2.0 μL |
| 25 × dNTP Mix (100 mM) | 0.8 μL |
| 10 × RT Random Primers/oligodT/specific primer | 2.0 μL |
| MultiScribe ™ Reverse Transcriptase | 1.0 μL |
| RNase Inhibitor | 1.0 μL |
| RNA | 2 μg |
| Nuclease-free H$_2$O | to 20.0 μL |

Reaction Condition

| | Step 1 | Step 2 | Step 3 | Step 4 |
|---|---|---|---|---|
| Temperature (° C.) | 25 | 37 | 85 | 4 |
| Time | 10 min | 120 min | 5 | ∞ |

The resulting cDNA was used as templates for subsequent PCR amplification using primers specific for interested genes. The PCR reaction was done as follows:

| | |
|---|---|
| cDNA | 1 μL |
| Ex PCR buffer | 5 μL |
| dNTP | 2 μL |
| ExTaq | 0.5 μL |
| P1 (25 pM) | 0.5 μL |
| P2 (25 pM) | 0.5 μL |
| ddH$_2$O | 40.5 μL |

Reaction Condition:

| | | |
|---|---|---|
| 94° C. | 3 min | |
| 94° C. | 30 s | ⎫ |
| 60° C. | 30 s | ⎬ 30 cycles |
| 72° C. | 1 min | ⎭ |
| 72° C. | 10 min | |

The resulting PCR product (10 μL) was ligated with pMD18-T vector. Top10 competent cells were transformed with 10 μL of the ligation product. Positive clones were checked by PCR using M13-48 and M13-47 primers followed by sequencing.

2. Humanized Antibody Molecule Construction

The rat anti-PD-1 antibody from hybridomas were selected and humanized according to the high affinity and specificity of anti-PD-1 antibody binding to PD-1, improving the homology with human antibody sequence. The said humanized usage is called as CDR-grafting technique. The variable region gene of antibody such as FR regions and CDR regions were divided by KABAT system and IMGT system. In antibody database, based on the alignments of binding sequence homology and structural similarity, the gene of murine region FR1-3 was replaced by humanized variable region FR1-3, region FR4 of the murine gene was replaced by humanized FR4 region derived from JH and JK genes which had the most similar structures. After verifying the template sequence and codon optimization, the heavy chain variable region and light chain variable region were synthesized and cloned into the expression vector, and then expressing the humanized antibody.

According to the binding ability to cell surface human and mouse PD-1, W3052_r16.88.9 and W3052_r16.81.3 was selected for humanization. Table. 2 shows the analysis of humanization scores. The clones W3052-16.88-z9-IgG4 (42720) was selected for affinity maturation considering all these factors such as better affinity and humanization scores (Table. 4).

TABLE 4

| Lead antibody | | FR1 | | FR2 | FR3 | FR4 | | Humanization score |
|---|---|---|---|---|---|---|---|---|
| W3052_r16.88.hAb140798 | WBP305_r16.88-hVH1-m | IGHV1-69*06 | 100% | 100% | 93.30% | IGHJ3*01 | 100% | 99.16% |
| | WBP305_r16.88-VL1 | IGKV2-29*02 | 100% | 100% | 100% | IGKJ2*01 | 100% | |
| W3052_r16.88.hAb240764 | WBP305_r16.88-hVH2 | IGHV1-69*06 | 100% | (IGHV1-8*01) 100% | 93.30% | IGHJ3*01 | 100% | 99.16% |
| | WBP305_r16.88-VL1 | IGKV2-29*02 | 100% | 100% | 100% | IGKJ2*01 | 100% | |
| W3052_r16.88.hAb340766 | WBP305_r16.88-hVH3 | IGHV1-69*06 | 100% | 85.70% | 93.30% | IGHJ3*01 | 100% | 97.38% |
| | WBP305_r16.88-VL1 | IGKV2-29*02 | 100% | 100% | 100% | IGKJ2*01 | 100% | |
| W3052_r16.88.hAb440770 | WBP305_r16.88-hVH1 | IGHV1-69*06 | 100% | 100% | 93.30% | IGHJ3*01 | 100% | 99.16% |
| | WBP305_r16.88-VL2 | IGKV2-30*01 | 100% | 100% | 100% | IGKJ2*01 | 100% | |
| W3052_r16.88.hAb540773 | WBP305_r16.88-hVH2-m | IGHV1-69*06 | 100% | (IGHV1-8*01) 100% | 93.30% | IGHJ3*01 | 100% | 99.16% |
| | WBP305_r16.88-VL2 | IGKV2-30*01 | 100% | 100% | 100% | IGKJ2*01 | 100% | |
| W3052_r16.88.hAb640800 | WBP305_r16.88-hVH3-m | IGHV1-69*06 | 100% | 85.70% | 93.30% | IGHJ3*01 | 100% | 97.38% |
| | WBP305_r16.88-VL2 | IGKV2-30*01 | 100% | 100% | 100% | IGKJ2*01 | 100% | |
| W3052_r16.88-z7-IgG442691 | WBP305_r16.88-hVH1 | IGHV1-69*06 | 100% | 100% | 100% | IGHJ3*01 | 100% | 100% |
| | WBP305_r16.88-VL1 | IGKV2-29*02 | 100% | 100% | 100% | IGKJ2*01 | 100% | |
| W3052_r16.88-z8-IgG442715 | WBP305_r16.88-hVH2 | IGHV1-69*06 | 100% | (IGHV1-8*01) 100% | 100% | IGHJ3*01 | 100% | 100% |
| | WBP305_r16.88-VL2 | IGKV2-30*01 | 100% | 100% | 100% | IGKJ2*01 | 100% | |
| W3052_r16.88-z9-IgG442720 | WBP305_r16.88-hVH3 | IGHV1-69*06 | 100% | 85.70% | 100% | IGHJ3*01 | 100% | 98.20% |
| | WBP305_r16.88-VL2 | IGKV2-30*01 | 100% | 100% | 100% | IGKJ2*01 | 100% | |
| W3052_r16.81.hAb140779 | WBP305_r16.81-VH1 | IGHV3-7*03 | 100% | 100% | 100% | IGHJ1*01 | 100% | 100% |
| | WBP305_r16.81-VL1 | IGKV1D-16*02 | 100% | 100% | 100% | IGKJ4*01 | 100% | |
| W3052_r16.81.hAb240781 | WBP305_r16.81-VH2 | IGHV3-9*01 | 100% | 100% | 100% | IGHJ1*01 | 100% | 100% |
| | WBP305_r16.81-VL1 | IGKV1D-16*02 | 100% | 100% | 100% | IGKJ4*01 | 100% | |
| W3052_r16.81.hAb340784 | WBP305_r16.81-VH1 | IGHV3-7*03 | 100% | 100% | 100% | IGHJ1*01 | 100% | 100% |
| | WBP305_r16.81-VL2 | IGKV1-39*01 | 100% | 100% | 100% | IGKJ4*01 | 100% | |
| W3052_r16.81.hAb440787 | WBP305_r16.81-VH2 | IGHV3-9*01 | 100% | 100% | 100% | IGHJ1*01 | 100% | 100% |
| | WBP305_r16.81-VL2 | IGKV1-39*01 | 100% | 100% | 100% | IGKJ4*01 | 100% | |

3. Affinity Maturation

Each amino acid of three complementary-determining regions (VH CDR3, VK CDR1, and VK CDR3) of parental clone was individually mutated to other 20 amino acids using a hybridization mutagenesis method. DNA primers containing a NNS codon encoding twenty amino acids were used to introduce mutation to each targeted CDR position. The individual degenerate primers were used in hybridization mutagenesis reactions. Briefly, each degenerate primer was phosphorylated, and then used in a 10:1 ratio with uridinylated ssDNA. The mixture was heated to 85° C. for 5 minutes then cooled down to 55° C. over 1 hour. Thereafter, T4 ligase and T4 DNA polymerase were added and mix was incubated for 1.5 hours at 37° C. Synthesis products for VH and VL CDRs were pooled respectively. Typically, 200 ng of the pooled library DNA was electroporated into BL21 for plaque formation on BL21 bacterial lawn or for production of scFv fragments.

The primary screen consisted of a single point ELISA (SPE) assay which was carried out using periplasmic extract (PE) of bacteria grown in 96-well plates (deep well). Briefly, this capture ELISA involved coating individual wells of a 96-well Maxisorp Immunoplate with anti-c-myc antibody in coating buffer (200 mM $Na_2CO_3$/$NaHCO_3$) at pH 9.2 overnight at 4° C. The next day, the plate was blocked with Casein for 1 h at room temperature. scFv PE was then added to the plate and incubated at room temperature for 1 hr. After washing, biotinylated antigen protein was added to the well and the mixture was incubated for 1 h at room temperature. This was followed by incubation with Streptavidin-HRP conjugate for 1 h at room temperature. HRP activity was detected with TMB substrate and the reaction was quenched with 2 M HCl. Plates were read at 450 nm. Clones exhibiting an optical density (OD) signal at 450 nm greater than the parental clone were picked and re-assayed by ELISA (as described above) in duplicate to confirm positive results. Clones that repeatedly exhibited a signal greater than that of the parental antibody were sequenced. The scFv protein concentration of each clone that had a CDR change was then determined by a quantitative scFv ELISA, where a scFv with known concentration was used as a reference. The scFv protein concentration was determined by comparing the ELISA signals with signals generated by the reference scFv. The binding assay was repeated once more for all positive variants under normalized scFv concentration in order to determine the relative binding affinity of the mutant scFv and the parental antibody.

The point mutations in VH and VL determined to be beneficial for binding to antigen were further combined to gain additional binding synergy. The combinatorial mutants were expressed as scFv and screened using the capture ELISA. Clones exhibiting an OD signal at 450 nm greater than the parental clone were sequenced and further confirmed by binding ELISA as described above.

Figure 2:
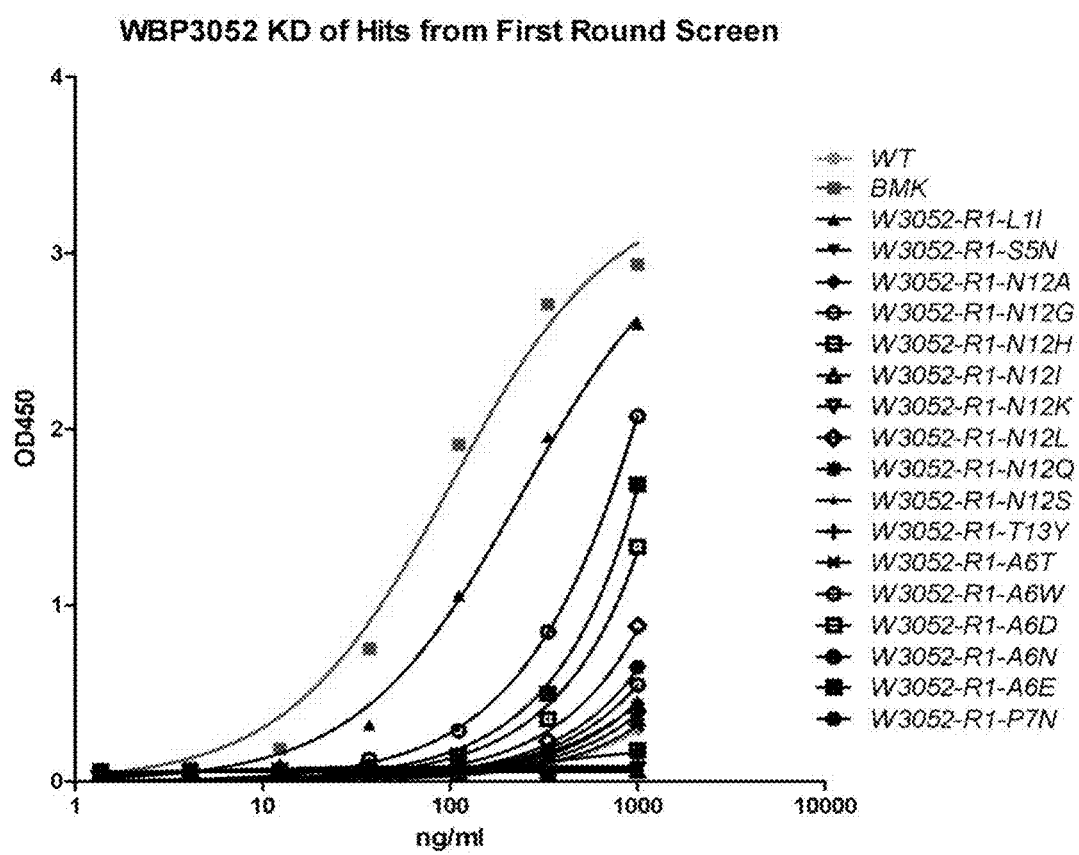
FIG. 2 shows the result from first around mutagenesis library screen. Sequence and analysis mutation on high affinity clones for the second around mutation.

After affinity maturation, a total of 10 humanized antibodies (2E5, 2G4, 1G10, 2C2, 2B1, 8C10, 1H6, 5C4, A6W and L1I) were obtained. FIG. 2 showed the result from first round mutagenesis library screen. Sequence and affinity data of 10 humanized antibodies in human, cynomolgus monkeys and mice were shown in Table 5.

Table. 5 showed the result from second round mutagenesis library screen. The clones 1H6, 2E5, 2G4 and 2C2 were selected for further analysis.

PBMC in a dose dependent way. The isotype was human IgG4 kappa. The same below.

1.2 Cross-Reactivity to Human, Cynomolgus and Mouse PD-1 (Cross-Species)

For ELISA, plates (Nunc) were coated with human, cynomolgus or mouse PD-1 (Sino Biological) at 1 µg/ml overnight at 4° C. After blocking and washing, antibodies were serially diluted in blocking buffer and added to the plates and incubated at room temperature for 1 h. The plates were then washed and subsequently incubated with secondary antibody goat anti human IgG HRP (Bethyl) for 1 h. After washing, TMB substrate was added and the reaction was stopped by 2 M HCl. The absorbance at 450 nm was read using a microplate reader (Molecular Device).

Figure 4:
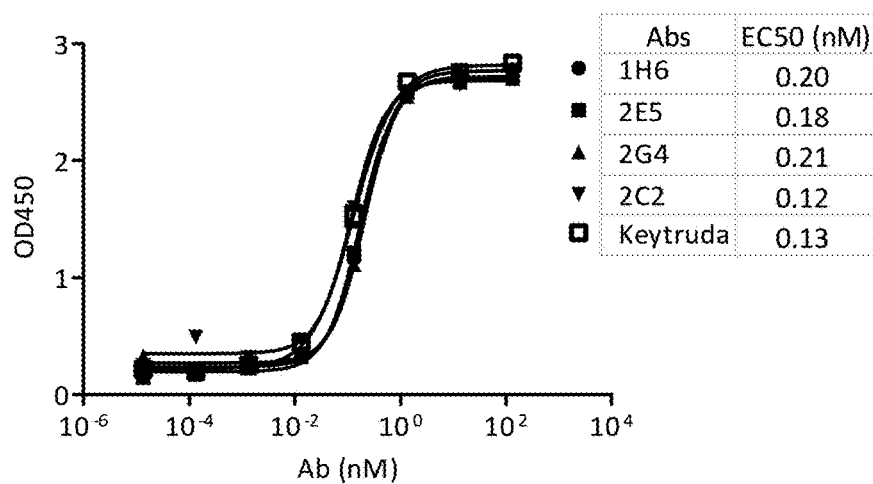
FIG. 4 shows the result of cross-species test by ELISA.
Figure 4:
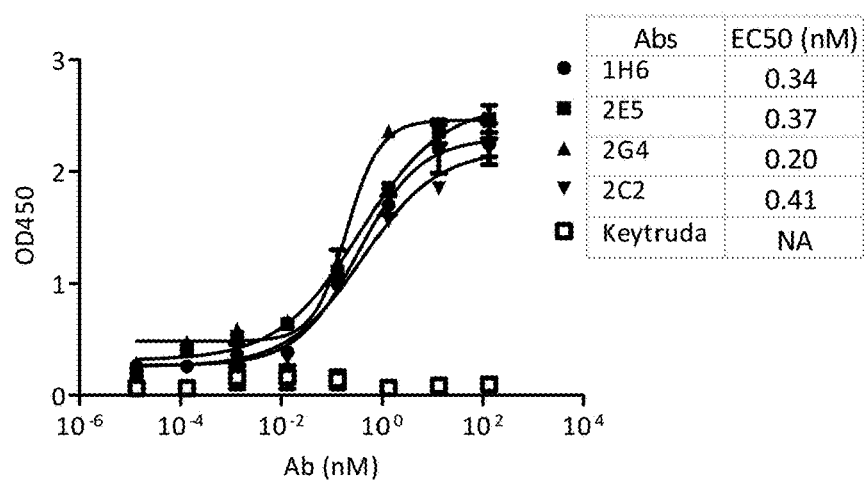
Figure 4:
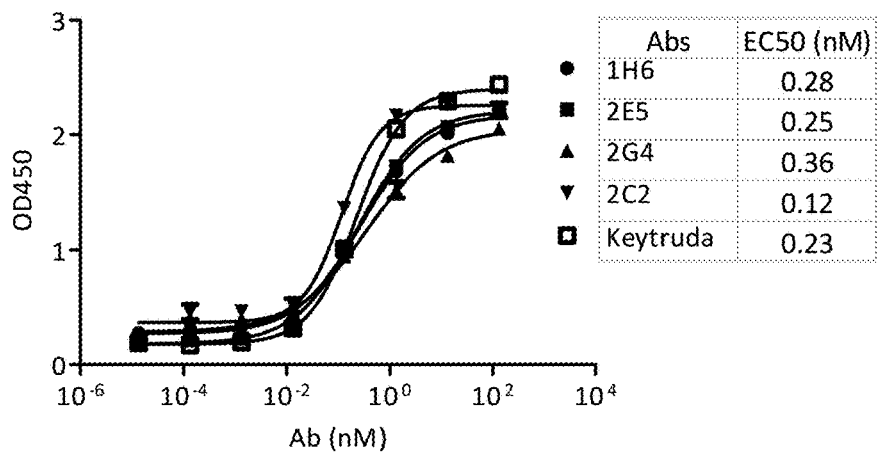

FIG. 4 showed the result of cross-species test by ELISA. FIG. 4A showed binding to human PD-1. FIG. 4B showed binding to mouse PD-1. FIG. 4C showed binding to cynomolgus PD-1.

2. Cross-Reactivity to Human PD-1 Family Members CD28, CTLA4

Constructed cell lines that respectively express human PD-1, CD28, CTLA-4 or ICOS were transferred in to 96-well U-bottom plates (BD) at a density of $2 \times 10^5$ cells/well. Testing antibodies were diluted in wash buffer (1×PBS/1% BSA) and incubated with cells at 4° C. for 1 h. After washing, the secondary antibody goat anti-human IgG Fc FITC (Jackson ImmunoResearch Lab) was added and incubated at 4° C. in the dark for 1 h. The cells were then washed

TABLE 5

| Name | VHCDR3 | VKCDR1 | VKCDR3 | Bmax (Human) | Kd (Human) | Bmax (Mouse) | Kd (Mouse) | Bmax (Cynomolgus) | Kd (Cynomolgus) |
|---|---|---|---|---|---|---|---|---|---|
| 2E5 | I | LDSDGGTYLYW | MQLTHWPYTFGQ | 3.279 | 0.0675 | 0.4696 | 0.0443 | 1.72 | 0.1088 |
| 2G4 | I | LDSDGSTYLYW | MQLTHWPYTFGQ | 3.371 | 0.0708 | 0.4793 | 0.0426 | 1.718 | 0.1057 |
| 1G10 | L | LDSDGATYLYW | MQLTHWPYTFGQ | 2.600 | 0.0711 | 0.2997 | 0.0718 | 1.082 | 0.1224 |
| 2C2 | I | LDSDGATYLYW | MQLTHWPYTFGQ | 3.175 | 0.082 | 0.416 | 0.049 | 1.668 | 0.116 |
| 2B1 | I | LDSDGNTYLYW | MQLTHWPYTFGQ | 3.019 | 0.0912 | 0.3393 | 0.0346 | 1.207 | 0.1142 |
| 8C10 | I | LDSDGQTYLYW | MQLTHENYTFGQ | 2.307 | 0.104 | 0.437 | 0.038 | 1.109 | 0.280 |
| 1H6 | L | LDSDGGTYLYW | MQLTHWNPYTFGQ | 3.348 | 0.1114 | 0.2213 | 0.0466 | 0.3171 | 0.0977 |
| 5C4 | L | LDSDGQTYLYW | MQLTHEPYTFGQ | 2.649 | 0.236 | 0.164 | 0.027 | 0.258 | 0.292 |
| A6W | L | LDSDGNTYLYW | MQLTHWPYTFGQ | 2.571 | 0.2885 | 0.1736 | 0.0294 | 0.0787 | 0.0016 |
| L1I | I | LDSDGNTYLYW | MQLTHAPYTFGQ | 1.048 | 1.8370 | 0.1048 | 0.0050 | 0.05175 | N/A |

4. Antibody Purification

The vector containing affinity matured humanized antibody were transfected into 293F cells for antibody production and expression. Antibodies in the supernatant of 293F cells were purified using Protein A affinity chromatography.

Example 4: Characterization of Humanized Antibody

1. Cross-Reactivity to Human, Cynomolgus and Mouse PD-1 (Cross-Species)
1.1 FACS Cross-reactivity was measured by FACS and ELISA. For FACS, the anti-PD-1 antibodies were tested binding to cell surface human, mouse and cynomolgus PD-1 as described in Example 2.3.

Figure 3:
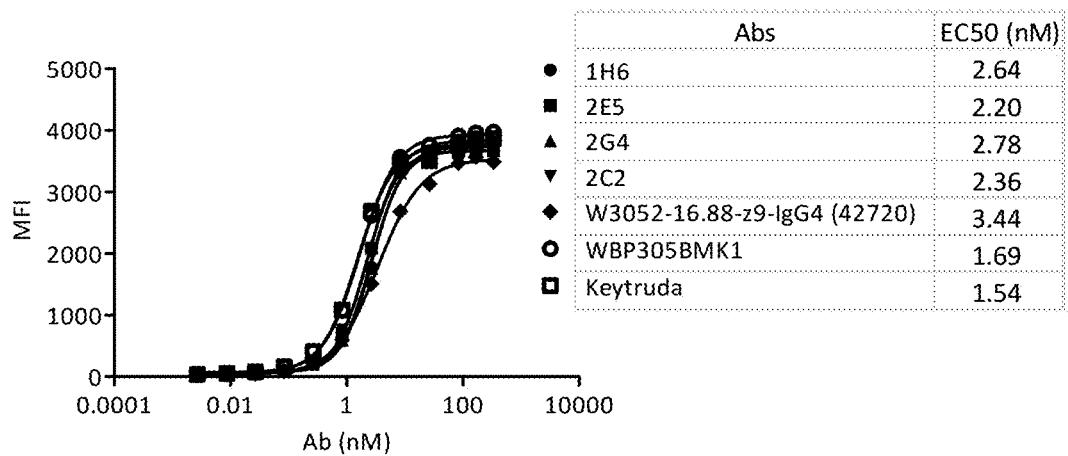
FIG. 3 shows the results of cross-species test by FACS.
Figure 3:
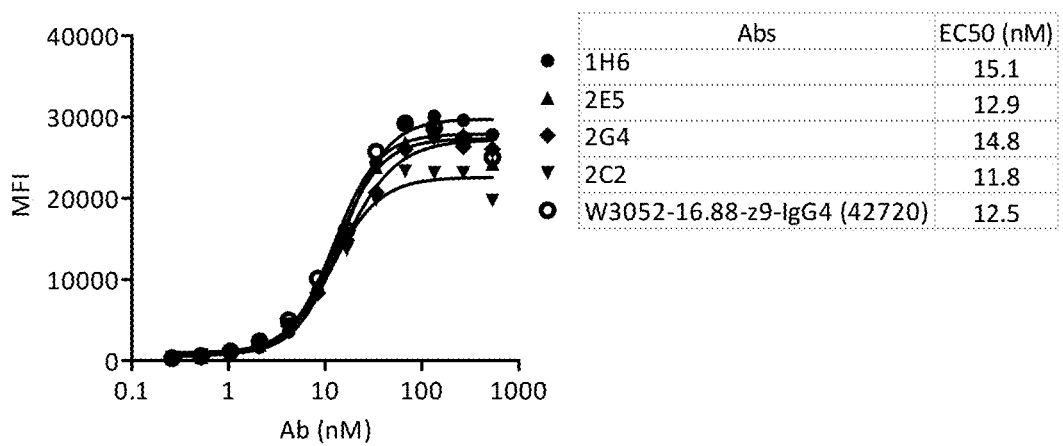
Figure 3:
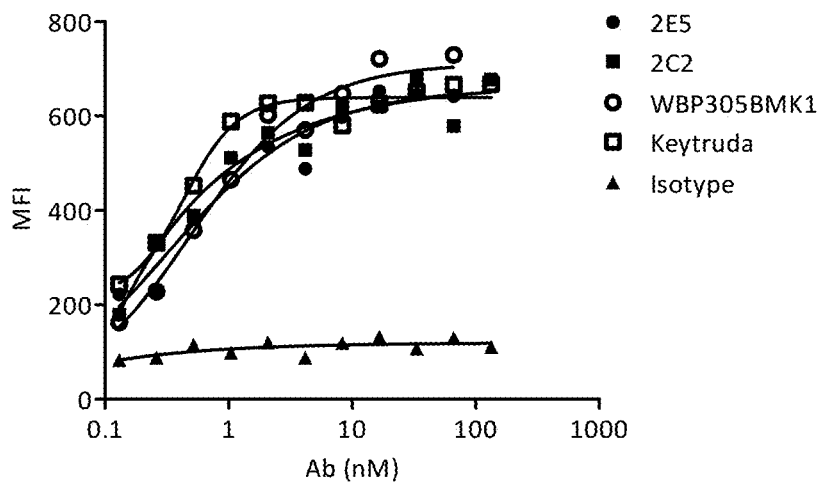

FIG. 3 showed the results of cross-species test by FACS. FIG. 3A showed binding to human PD-1 transfected CHO-S cells. The antibodies can bind specifically to the human PD-1 with EC50 of 2.20-2.78 nM. FIG. 3B showed binding to mouse PD-1 transfected 293F cells. The antibodies can bind specifically to the mouse PD-1 with EC50 of 11.8-15.1 nM. FIG. 3C showed binding to activated cynomolgus once and resuspended in 1×PBS/1% BSA, and analyzed by flow cytometery (BD) and FlowJo software.

Figure 5:
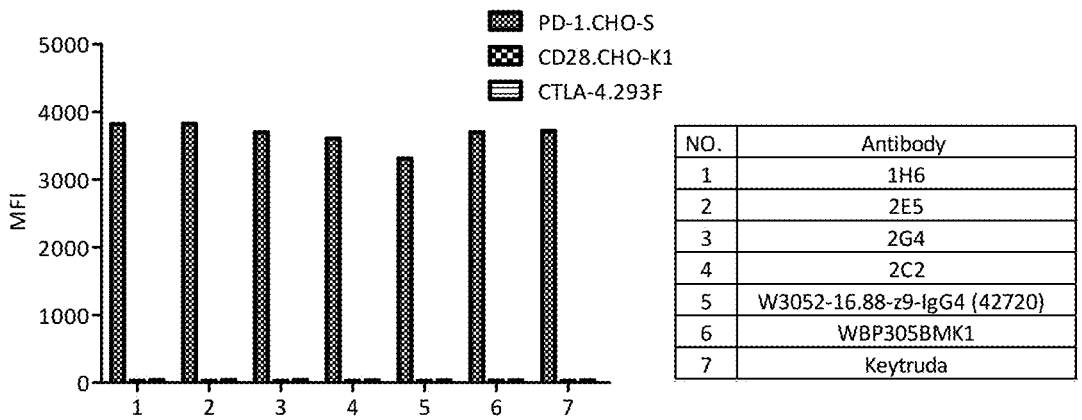
FIG. 5 shows the result of cross-family test. The anti-PD-1 antibodies bind specifically to human PD-1, but not to CD28 and CTLA-4.

FIG. 5 showed the result of cross-family test. The anti-PD-1 antibodies can bind specifically to human PD-1, but not to CD28 and CTLA-4.

3. Blocking of Ligand Binding to PD-1

3.1 The ability of anti-PD-1 antibodies to block PD-L1 binding to PD-1 was tested by FACS as described in Example 2.3.

3.2 The ability of anti-PD-1 antibodies to block PD-L2 binding to PD-1 was tested by ELISA. Briefly, plates (Nunc) were coated with human PD-1 at 1 µg/ml overnight at 4° C. Antibodies were serially diluted in blocking buffer and mixed with his tag conjugated PD-L2. After blocking and washing the coated plates, the antibody/PD-L2 mixture were added to the plates, then incubated at room temperature for 1 h. The plates were then washed and subsequently incubated with secondary antibody goat anti-his HRP (GenScript) for 1 h. After washing, TMB substrate was added and the reaction was stopped by 2 M HCl. The absorbance at 450 nm was read using a microplate reader (Molecular Device).

Figure 6:
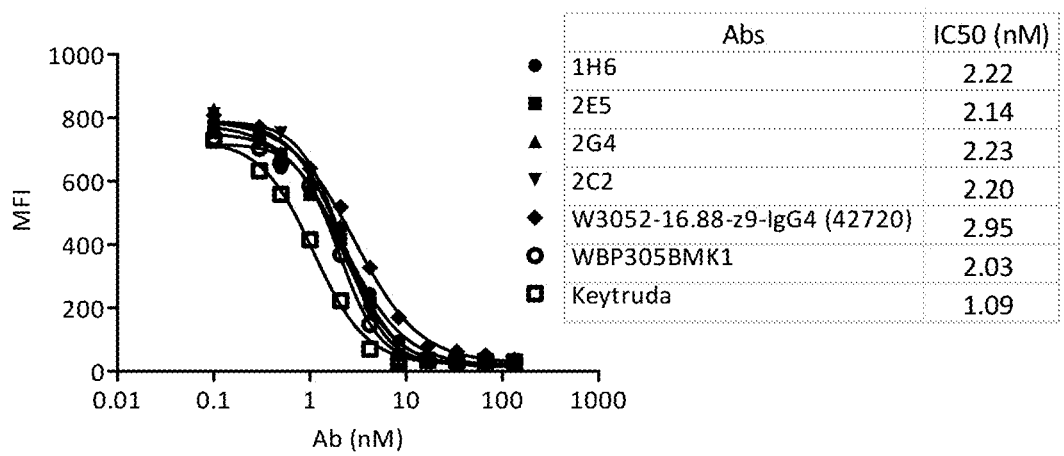
FIG. 6A shows the result of anti-PD-1 antibodies blocking human PD-L1 binding to PD-1 transfected CHO-S cells.
FIG. 6B shows the result of anti-PD-1 antibodies blocking mouse PD-L1 binding to PD-1 transfected 293F cells.
Figure 6:
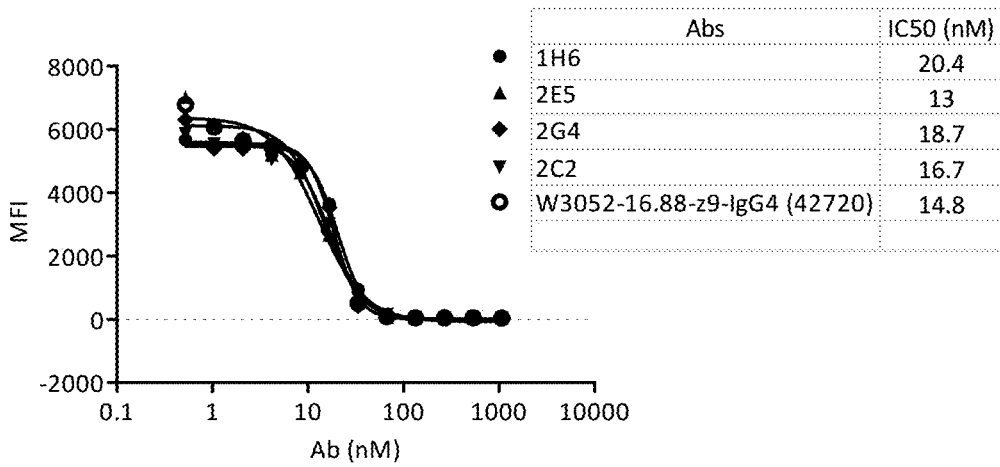

FIG. 6A showed the result of anti-PD-1 antibodies blocking human PD-L1 binding to PD-1 transfected CHO-S cells.

Figure 7:
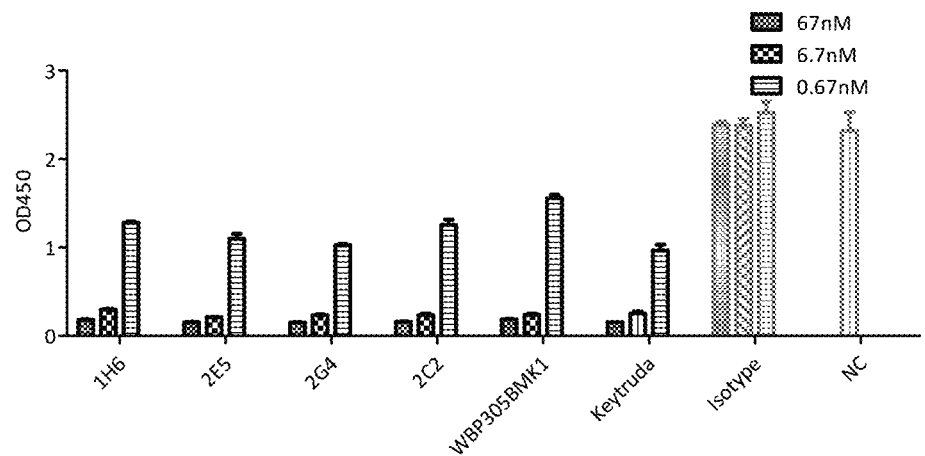
FIG. 7 shows that the anti-PD-1 antibodies could block human PD-L2 binding to PD-1.

FIG. 6B shows the result of anti-PD-1 antibodies blocking mouse PD-L1 binding to PD-1 transfected 293F cells. FIG. 7 showed that the anti-PD-1 antibodies could block human PD-L2 binding to PD-1 in a dose-dependent manner.

4. Full Kinetic Binding Affinity Tested by Surface Plasmon Resonance (SPR) Antibodies were characterized for affinity and binding kinetics to PD-1 by SPR assay using ProteOn XPR36 (Bio-Rad). Protein A protein (Sigma) was immobilized to a GLM sensor chip (Bio-Rad) through amine coupling. Purified antibodies were flowed over the sensor chip and captured by the Protein A. The chip was rotated 90° and washed with running buffer (1×PBS/0.01% Tween20, Bio-Rad) until the baseline was stable. Seven concentrations of human PD-1 and running buffer were flowed through the sensor chip at a flow rate of 30 µL/min for an association phase of 180 s, followed by 300 s dissociation. After regeneration, seven concentration of mouse PD-1 and running buffer were flowed through the sensor chip at a flow rate of 30 µL/min for an association phase of 180 s, followed by 300 s dissociation. The chip was regenerated with pH 1.5 $H_3PO_4$ after each run. The association and dissociation curve was fit by 1:1 Langmuir binding model using ProteOn software.

Table. 6A-6B showed the results of full kinetic binding affinity to human and mouse PD-1 by SPR. WBP305BMK1 was synthesized according to the clone of 5C4 from BMS U.S. Pat. No. 9,084,776B2. Keytruda was the anti-PD-1 drug from Merck. The same below. The results showed that the affinity ability to human PD-1 by SPR assay was from 1.43E-8 to 5.64E-9 mol/L. Comparing WBP305BMK1 with Keytruda, the $K_D$ value of antibody 2E5, 2G4 or 2C2 was much smaller, illustrating that 2E5, 2G4 or 2C2 had better binding ability to human PD-1. In addition, the affinity ability to mouse PD-1 was from 9.37E-9 to 3.89E-9 mol/L.

cells were then washed once and resuspended in 1×PBS/1% BSA, and analyzed by flow cytometry (BD). Fluorescence intensity was converted to bound molecules/cell based on the quantitative beads (Quantum™ MESF Kits, Bangs Laboratories, Inc.). $K_D$ was calculated using Graphpad Prism5.

Table. 7A-7B show the results of binding affinity of anti-PD-1 antibodies to cell surface human and mouse PD-1 molecules tested by flow cytometry. The results showed that the affinity ability to human PD-1 by FACS assay was from 3.80E-10 to 2.15E-10 mol/L. In addition, the affinity ability to mouse PD-1 was from 5.39E-8 to 1.74E-8 mol/L.

TABLE 7A

| Sample | Best fit-KD (M) |
|---|---|
| 1H6 | 2.15E−10 |
| 2E5 | 2.30E−10 |
| 2G4 | 3.80E−10 |
| 2C2 | 2.64E−10 |
| W3052-16.88.z9-IgG4 (42720) | 4.32E−10 |
| WBP305BMK1 | 2.62E−10 |
| Keytruda | 1.79E−10 |

TABLE 7B

| Sample | Best fit-KD (M) |
|---|---|
| 1H6 | 5.39E−08 |
| 2E5 | 2.90E−08 |
| 2G4 | 3.51E−08 |
| 2C2 | 1.74E−08 |
| W3052-16.88.z9-IgG4 (42720) | 1.67E−08 |

TABLE 6A

| Analyte | Ligand | ka (1/Ms) | kd (1/s) | KD (M) | Chi$^2$ (RU$^2$) | U-value |
|---|---|---|---|---|---|---|
| hPD-1.His | 1H6 | 6.44E+05 | 9.18E−03 | 1.43E−08 | 0.05 | 1 |
| | 2E5 | 5.97E+05 | 3.66E−03 | 6.13E−09 | 0.14 | 1 |
| | 2G4 | 6.63E+05 | 4.70E−03 | 7.09E−09 | 0.10 | 1 |
| | 2C2 | 7.33E+05 | 4.14E−03 | 5.64E−09 | 0.03 | 1 |
| | W3052-16.88.z9-IgG4 (42720) | 3.82E+06 | 1.36E−01 | 3.56E−08 | 0.03 | 5 |
| | WBP305BMK1 | 4.02E+05 | 1.35E−03 | 3.37E−09 | 0.01 | 1 |
| | Keytruda | 8.79E+05 | 2.28E−03 | 2.59E−09 | 0.07 | 1 |

TABLE 6B

| Analyte | Ligand | ka (1/Ms) | kd (1/s) | KD (M) | Chi$^2$ (RU$^2$) | U-value |
|---|---|---|---|---|---|---|
| mPD-1.His | 1H6 | 3.20E+05 | 3.00E−03 | 9.37E−09 | 0.06 | 1 |
| | 2E5 | 3.23E+05 | 1.29E−03 | 3.99E−09 | 0.01 | 1 |
| | 2G4 | 3.34E+05 | 1.30E−03 | 3.89E−09 | 0.01 | 1 |
| | 2C2 | 2.21E+05 | 1.53E−03 | 6.92E−09 | 0.19 | 1 |
| | W3052-16.88.z9-IgG4 (42720) | 1.95E+05 | 8.09E−03 | 4.16E−08 | 0.01 | 1 |

5. Binding Affinity of Anti-PD-1 Antibodies to Cell Surface PD-1 Molecules Tested by Flow Cytometry (FACS)

CHO-S cells expressing human PD-1 or 293F cells expressing mouse PD-1 were transferred in to 96-well U-bottom plates (BD) at a density of 1×10$^5$ cells/well. Testing antibodies were 1:2 serially diluted in wash buffer (1×PBS/1% BSA) and incubated with cells at 4° C. for 1 h. The secondary antibody goat anti-human IgG Fc FITC (3.0 moles FITC per mole IgG, (Jackson Immunoresearch Lab) was added and incubated at 4° C. in the dark for 1 h. The 6. Epitope Binning Test The binding epitope of anti-PD-1 antibodies was compared with benchmark antibody A and B by FACS. CHO-S cells expressing human PD-1 on the cell surface were incubated with mixture of biotinylated benchmark antibody A or B (1 µg/ml) and testing antibodies (serially diluted in wash buffer) at 4° C. for 1 h. The cells were washed and the second antibody Streptavidin-PE were added and incubated for 30 min at 4° C. The cells were then washed once and resuspended in 1×PBS/1% BSA, and analyzed by flow cytometry (BD).

Figure 8:
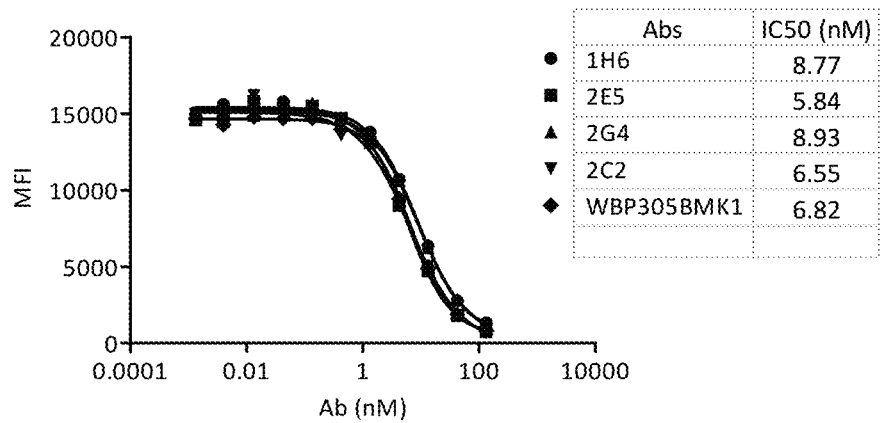
FIG. 8A-8B show the results of epitope binning assay suggesting that the anti-PD-1 antibodies are in the same or close epitope bin as benchmark antibodies.
Figure 8:
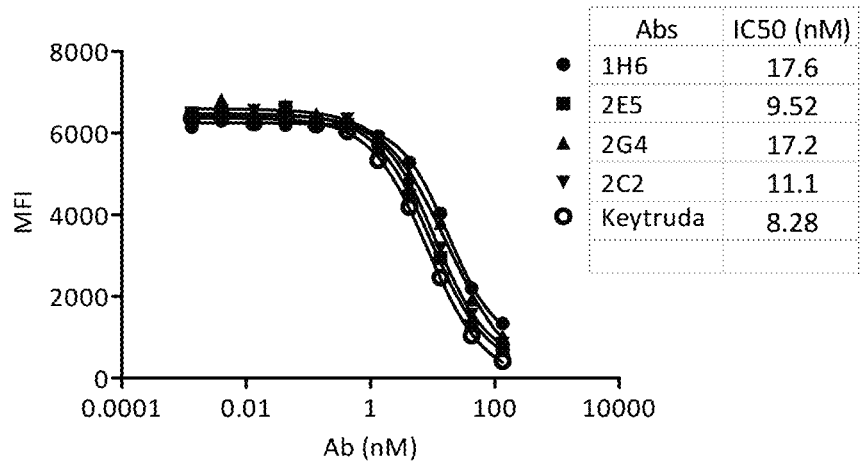

FIG. 8A-8B showed the results of epitope binning assay suggesting that the anti-PD-1 antibodies are in the same or close epitope bin as benchmark antibodies. FIG. 8A showed binning against WBP305BMK1 (U.S. Pat. No. 9,084,776). FIG. 8B showed binning against Keytruda (U.S. Pat. No. 8,168,757).

Furthermore, alanine scanning experiments on hPD-1 were conducted and their effect to antibody binding was evaluated. Alanine residues on hPD-1 were mutated to glycine codons, and all other residues were mutated to alanine codons. For each residue of the hPD-1 extracellular domain (ECD), point amino acid substitutions were made using two sequential PCR steps. A pcDNA3.3-hPD-1_ECD.His plasmid that encodes ECD of human PD-1 and a C-terminal His-tag was used as template, and a set of mutagenic primer was used for first step PCR using the QuikChange lightning multisite-directed mutagenesis kit (Agilent technologies, Palo Alto, Calif.). Dpn I endonuclease was used to digest the parental template after mutant strand synthesis reaction. In the second-step PCR, linear DNA expression cassette which composed of a CMV promoter, an extracellular domain (ECD) of PD-1, a His-tag and a herpes simplex virus thymidine kinase (TK) polyadenylation was amplified and transiently expressed in HEK293F cells (Life Technologies, Gaithersburg, Md.).

Monoclonal antibodies W3052_r16.88.9 and Keytruda were coated in plates for ELISA binding assay. After interacting with the supernatant that contains quantified PD-1 mutant or human/mouse PD-1 ECD.His protein (Sino Biological, China), HRP conjugated anti-His antibody was added as detection antibody. Absorbance was normalized according to the average of control mutants. After setting an additional cutoff to the binding fold change (<0.55), the final determined epitope residues were identified.

Figure 9:
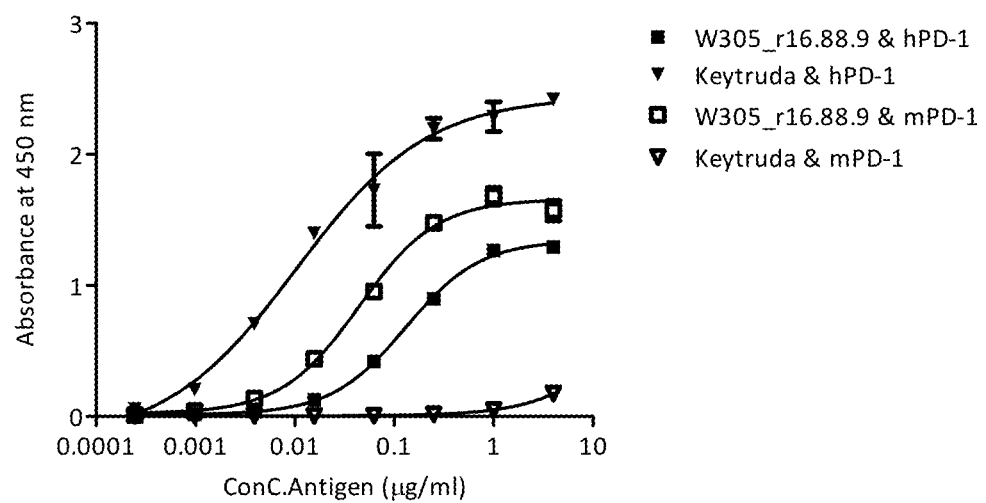
FIG. 9 shows the cross-reactivity of anti-PD-1 antibodies with human/mouse PD-1. 2 μg/mL of each antibody were coated at 96-well plate overnight and incubated with hPD-1/mPD-1-His protein, then HRP-anti-His antibody were added for detection.

The binding activities of the antibodies W3052_r16.88.9 and Keytruda to both human and murine PD-1 were conducted (FIG. 9). W3052_r16.88.9 was found binding to both hPD-1 and mPD-1 while Keytruda only bound to the human one (FIG. 9). This unique functional cross-reactivity of W3052_r16.88.9 can help provide more animal model options in preclinical studies when evaluating the drug safety. To explore the origin of the observed binding behaviors, epitope mapping of both antibodies were conducted.

Top 30 point-substituted hPD-1 mutants that significantly reduced antibody binding were shown in Table 8. Checking the positions of all these residues on the hPD-1 crystal structures (PDB code 3RRQ and 4ZQK) revealed that some amino acids (e.g. Val144, Leu142, Val110, Met108, Cys123 etc.) were fully buried in the protein, and were unlikely to directly contact any antibodies. The observed binding reductions most probably resulted from the instability or even collapse of hPD-1 structure after alanine substitutions. According to the antigen structure analysis, some of the residues don't involve binding activity, but are expected to respond to the stability of the hPD-1 structure, e.g. V144 and L142. Mutants that affect both antibodies were treated as false hot spots and were removed from the list. After setting an additional cutoff to the binding fold change (<0.55), the final determined epitope residues were listed in Table 9. They are 9 positions to W3052_r16.88.9 and 5 positions to Keytruda.

Figure 10:
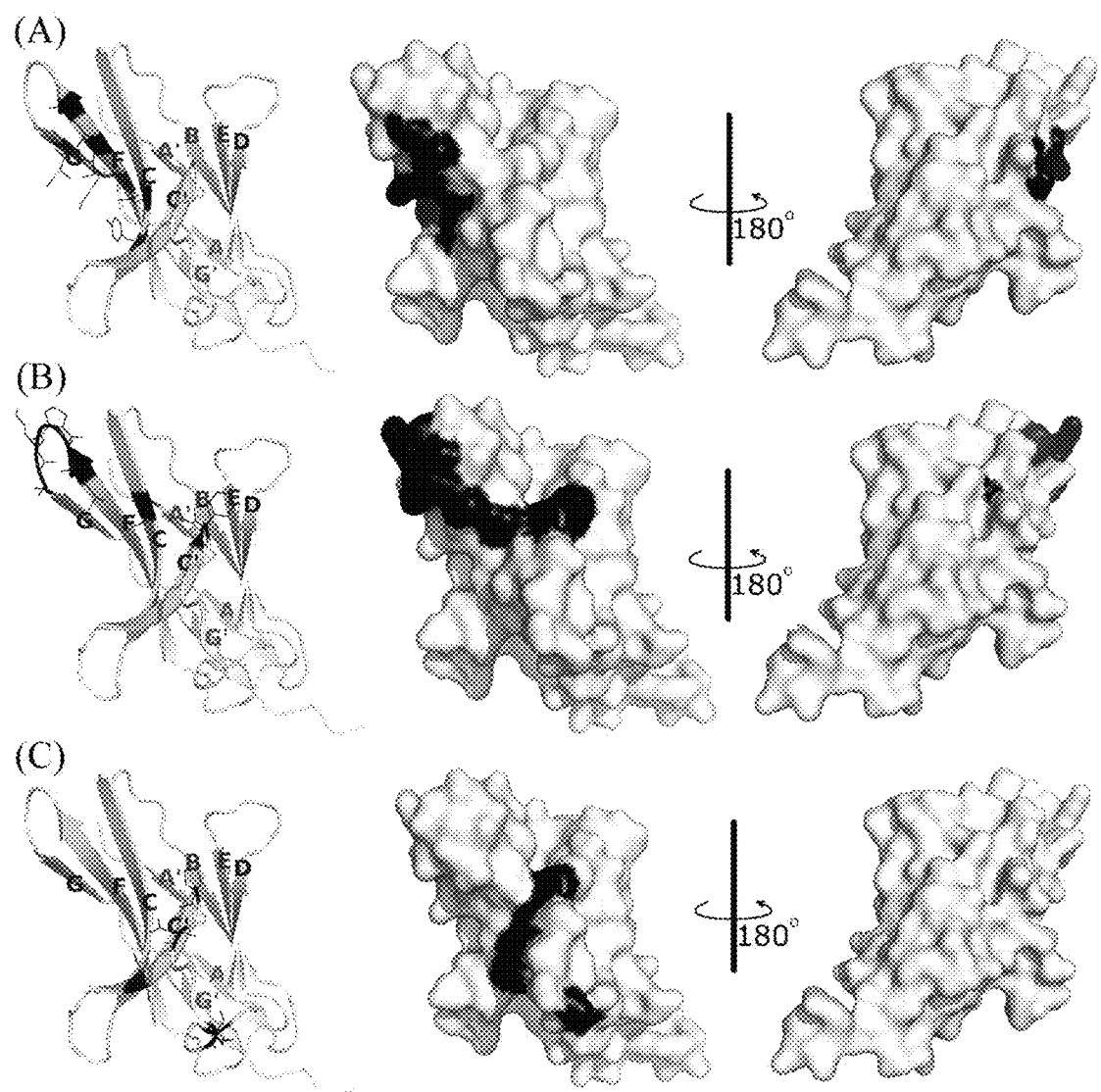
FIG. 10 shows the Hot spot residues mapped on hPD-1 structure. (A). hPD-L1 binding site. Data were obtained from the literature Zak et al. 2015. (B-C). Binding site of antibody W3052_r16.88.9 and Keytruda, respectively. Data were from table 8. Colors on the pictures are to help distinguish the differences between epitopes.

Comparing the epitope residues of W3052_r16.88.9 and Keytruda in Table 9 only revealed two overlapped hot spot residues. The rest looked quite diverse, which indicated that two antibodies might have adopted very different mechanisms in terms of hPD-1 binding and hPD-L1 blocking. Reading the residue IDs in Table 9 is not straightforward to interpret the mechanisms. All data in Table 9, as well as the hPD-L1 binding site, were therefore mapped on the crystal structure of hPD-1 to make a better visualization and comparison. (FIG. 10).

TABLE 8

The effect of PD-1 point mutations on antibody binding

| | W3052_r16.88.9 | | | Keytruda | |
|---|---|---|---|---|---|
| PD-1 #Residue | fold change[a] | SD | PD-1 #Residue | fold change[a] | SD |
| V 144 | 0.09 | 0.01 | P 89 | 0.18 | 0.02 |
| L 142 | 0.21 | 0.01 | D 85 | 0.38 | 0.01 |
| K 131 | 0.27 | 0.02 | V 144 | 0.4 | 0.01 |
| P 35 | 0.31 | 0 | R 94 | 0.46 | 0.04 |
| A 129 | 0.34 | 0 | F 106 | 0.47 | 0.05 |
| V 64 | 0.34 | 0 | K 78 | 0.48 | 0 |
| P 83 | 0.38 | 0.03 | P 83 | 0.5 | 0.01 |
| L 128 | 0.39 | 0.01 | D 92 | 0.5 | 0.02 |
| S 137 | 0.42 | 0.01 | P 39 | 0.54 | 0 |
| F 95 | 0.42 | 0.01 | A 81 | 0.57 | 0.01 |
| P 130 | 0.44 | 0.01 | C 123 | 0.57 | 0.01 |
| C 123 | 0.44 | 0.01 | N 66 | 0.57 | 0.03 |
| R 94 | 0.49 | 0.04 | L 142 | 0.59 | 0.01 |
| M 108 | 0.49 | 0.02 | F 82 | 0.61 | 0.03 |
| D 117 | 0.51 | 0.01 | F 95 | 0.61 | 0.04 |
| F 82 | 0.53 | 0.02 | F 52 | 0.63 | 0.01 |
| A 132 | 0.54 | 0.02 | M 108 | 0.64 | 0.06 |
| V 110 | 0.54 | 0.02 | L 128 | 0.68 | 0.01 |
| N 49 | 0.55 | 0.01 | I 126 | 0.72 | 0.01 |
| W 67 | 0.55 | 0.01 | A 113 | 0.72 | 0.01 |
| E 61 | 0.56 | 0.04 | V 110 | 0.73 | 0.04 |
| N 102 | 0.57 | 0.04 | G 47 | 0.73 | 0.01 |
| P 39 | 0.57 | 0.01 | D 117 | 0.73 | 0.07 |
| I 126 | 0.59 | 0.04 | N 49 | 0.73 | 0 |
| A 113 | 0.6 | 0.01 | S 87 | 0.74 | 0.06 |
| F 52 | 0.61 | 0.02 | L 42 | 0.76 | 0.01 |
| H 155 | 0.62 | 0.04 | N 102 | 0.76 | 0.01 |
| R 86 | 0.64 | 0.08 | W 67 | 0.81 | 0.01 |
| A 149 | 0.64 | 0 | P 101 | 0.81 | 0.04 |
| G 47 | 0.64 | 0.03 | A 80 | 0.82 | 0.01 |

[a]Fold change in binding is relative to the binding of several silent alanine substitutions.

TABLE 9

Identification of potential epitopes

| PD-1 to r16.88.9 | residue location | PD-1 to Keytruda | residue location |
|---|---|---|---|
| P 35 | A | K 78 | C' |
| V 64 | C | P 83 | C' |
| F 82 | C' | D 85 | C" |
| P 83 | C' | P 89 | C" |
| L 128 | FG | D 92 | C"D |
| A 129 | FG | | |
| P 130 | FG | | |
| K 131 | FG | | |
| A 132 | FG | | |

Cutoff: fold change <0.55
* The C" strand observed on mPD-1 does not exist on hPD-1 structure. This β-sheet is replaced by a structreless loop on hPD-1. We still use C" to label this region, just for the purpose of easier comparison to mPD-1.

Figure 11:
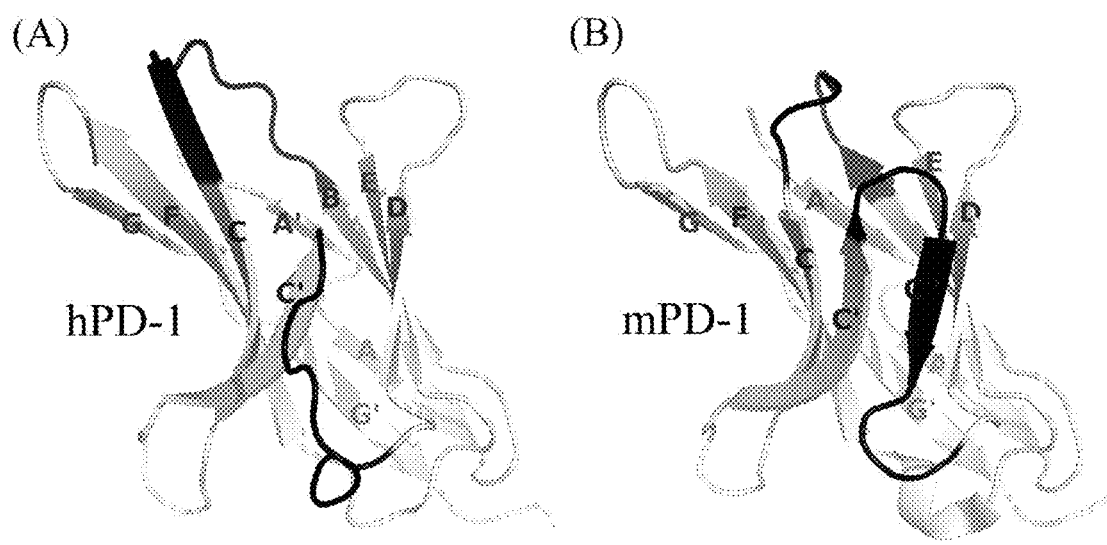
FIG. 11 shows comparison between human and murine PD-1. Their obvious structural differences (BC loop and C'D loop (or C" strand on mPD-1)) were marked in orange color. (A). Structures of hPD-1 (PDB code 4ZQK). The missing loop (Asp85-Asp92) were remolded based on its NMR structures (PDB code 2M2D). (B). Structure of mPD-1 (PDB code 3BIK).

Two investigated antibodies W3052_r16.88.9 and Keytruda, although both are functional in binding hPD-1 and blocking hPD-L1, have obviously different epitopes (FIG. 10B, 10C). The epitope of Keytruda were mainly contributed by the residues on the C'D loop (corresponding to the C" strand on mPD-1), which didn't intersect the PD-L1 binding site at all. This suggested the hPD-L1 blocking function of Keytruda relied more on its steric hindrance effects provided by the size of the antibody. In contrast, the epitope mapping results show that the epitope of antibody W3052_r16.88.9 was composed of hot spots distributed across multiple locations, and have direct overlap with the hPD-L1 binding site (FIG. 10A, 10B). W3052_r16.88.9 blocked hPD-L1 by means of competing with hPD-L1 in reacting to their common binding site. What's more, W3052_r16.88.9 had no interactions with the flexible C'D loop (or the corresponding C" strand on mPD-1), where human and murine PD-1 show big structural deviations (FIG. 11). Its binding site is mostly located on the FG loop (Lin et al. (2008) PNAS 105: 3011-3016). That explains why W3052_r16.88.9 can bind to both PD-1 species while Keytruda only binds to the human one (FIG. 9). Because of this unique functional cross-reactivity, the preclinical safety evaluations of W3052_r16.88.9 could be conducted in mouse model, which will greatly simplify and accelerate the development. Overall, antibody W3052_r16.88.9 is expected to be more functional and developable than Keytruda.

7. In Vitro Function of Anti-PD-1 Antibodies Tested by Cell-Based Assays 7.1 Mixed Lymphocyte Reaction (MLR) was used to test the effects of anti-PD-1 antibodies on T lymphocytes function Human DCs, $CD4^+$ T, $CD8^+$ T and total T cells isolation: Human PBMCs were freshly isolated from healthy donors using Ficoll-Paque PLUS (GE) gradient centrifugation. Monocytes were isolated using Human Monocyte Enrichment Kit (StemCell) according to the manufacturer's instructions. Cells were cultured in medium containing rhGM-CSF and rhIL-4 for 5 to 7 days to generate dendritic cells. 18 to 24 hours before MLR, 1 μg/mL LPS was added to the culture to induce the maturation of the DCs. Human $CD4^+$ T cells were isolated using Human $CD4^+$ T Cell Enrichment Kit (StemCell) according to the manufacturer's protocol. Mouse $CD4^+$ T cells were obtained from the spleen of Balb/c mouse using Mouse $CD4^+$ T Cell Isolation Kit (StemCell) according to the manufacturer's protocol. Mouse DCs were induced from bone marrow cells of C57BL/6 mouse in medium containing rmGM-CSF and rmIL-4 for 5 to 7 days. 18 to 24 hours before MLR, 1 μg/mL LPS was added to the culture to induce the maturation of the DCs.

Briefly, primary dendritic cell (DC)-stimulated MLR was conducted in 96-well, U-bottom tissue culture plates in 200 μL of RPMI 1640 containing 10% FCS and 1% antibiotics. DCs were mixed with $1 \times 10^5$ $CD4^+$ T cells at a ratio between 1:10 and 1:200 DC: T cells in the presence or absence of testing antibodies or benchmark antibodies (form 166.75 nM down to 0.00667 nM, generally total six concentrations). To determine the effect of anti-PD-1 antibodies on T cell function, the cytokine production and T cell proliferation were determined. Results shown are representative of a minimum of five experiments performed.

Cytokine detection: Human IFN-γ and IL-2 were measured by enzyme-linked immunosorbent assay (ELISA) using matched antibody pairs. The plates were pre-coated with capture antibody specific for human IFN-γ (cat# Pierce-M700A) or IL-2 (cat# R&D-MAB602), respectively. The biotin-conjugated anti-IFN-γ antibody (cat# Pierce-M701B) or anti-IL-2 antibody (cat# R&D-BAF202) was used as detecting antibody.

Figure 12:
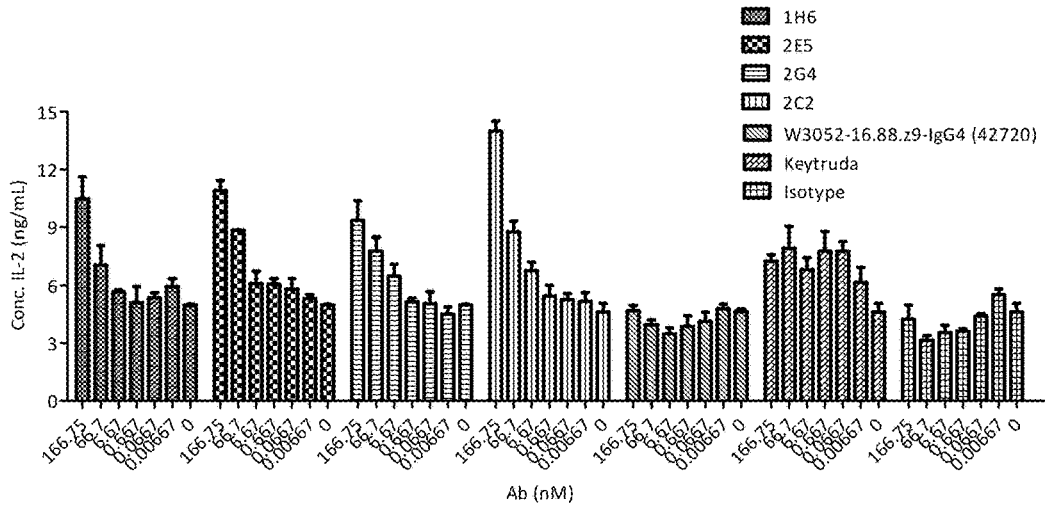
FIG. 12A-12C show the results of human allo-MLR demonstrating the anti-PD-1 antibodies can enhance the function of human CD4+ T cell.
Figure 12:
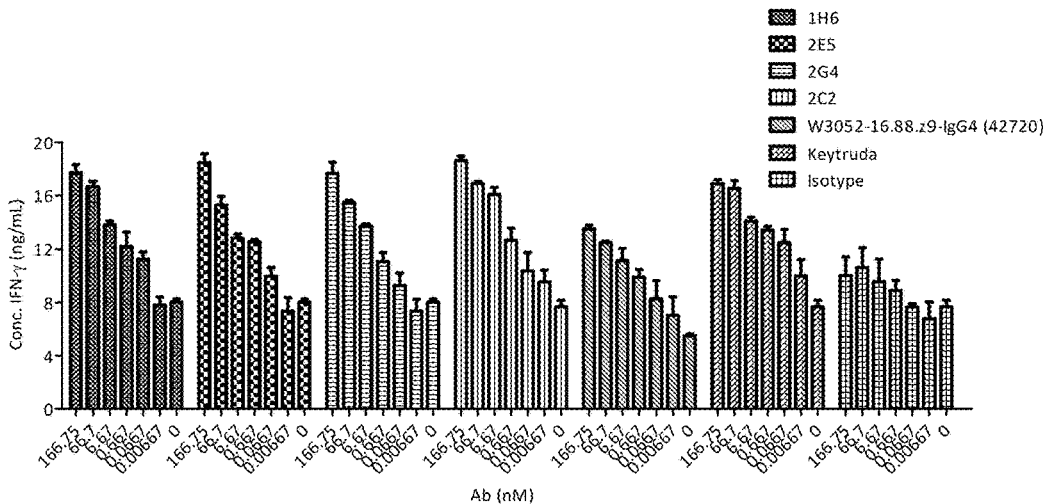
Figure 12:
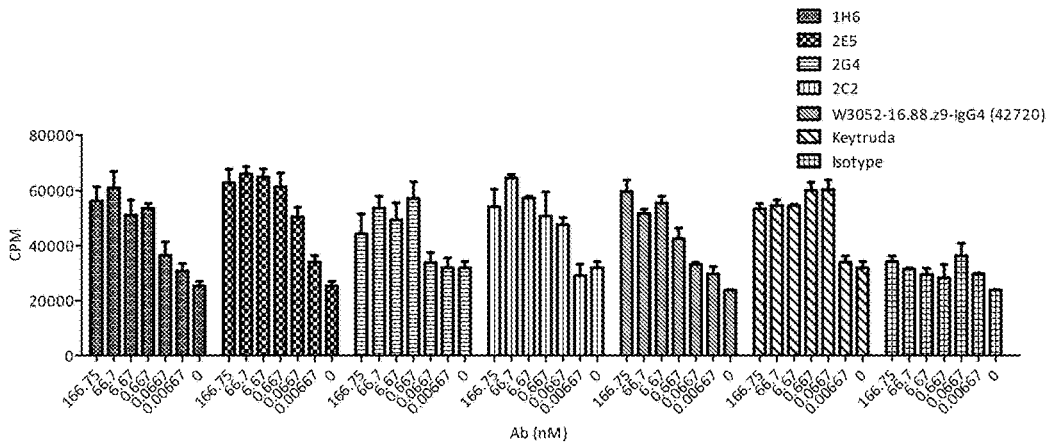

FIG. 12A showed anti-PD-1 antibodies increased IL-2 secretion in a dose-dependent manner. FIG. 12B shows anti-PD-1 antibodies increase IFN-γ secretion in a dose-dependent manner.

Proliferation assay: 3H-thymidine (cat# PerkinElmer-NET027001MC) was diluted 1:20 in 0.9% NaCl solution, and added to the cell culture plates at 0.5 uCi/well. The plates were cultured in 5% $CO_2$ at 37° C. for 16 to 18 hours, before the incorporation of 3H-thymidine into the proliferating cells was determined. FIG. 12C shows anti-PD-1 antibodies increase $CD4^+$ T cells proliferation in a dose-dependent manner.

Figure 13:
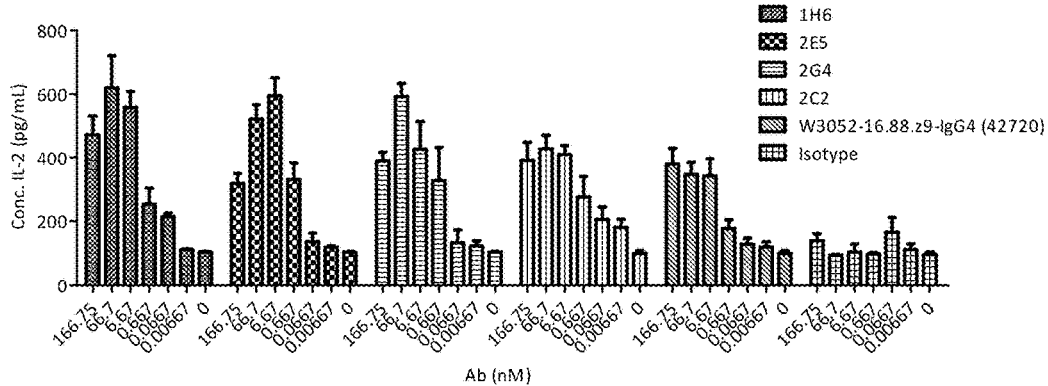
FIG. 13A-13C show the results of mouse allo-MLR demonstrating that the anti-PD-1 antibodies can enhance the function of mouse CD4+ T cell.
Figure 13:
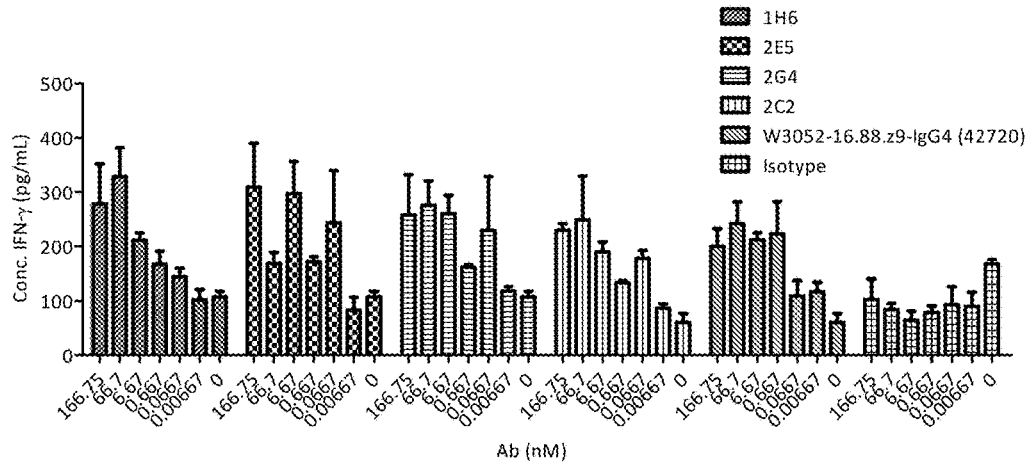
Figure 13:
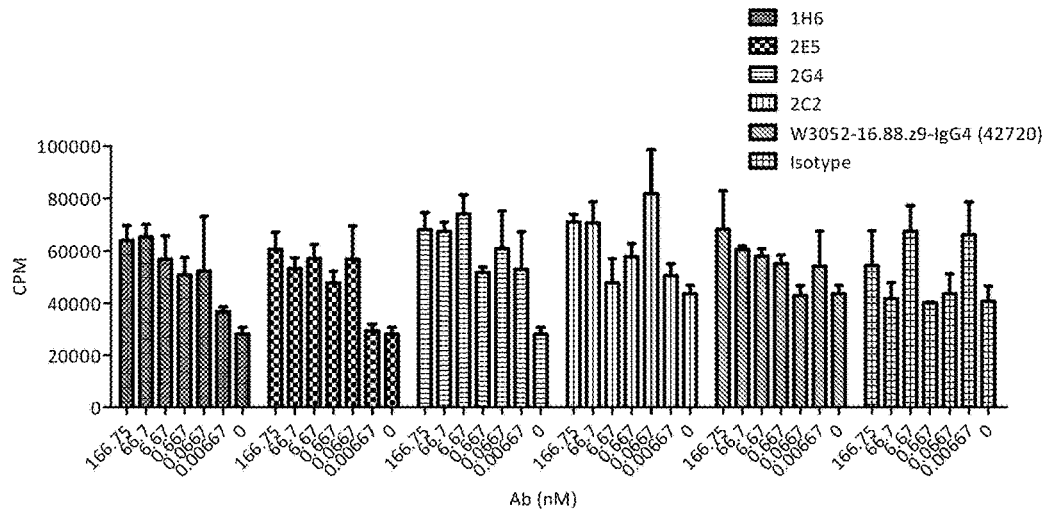

To determine the effect of anti-PD-1 antibodies on mouse T cell function, the cytokine production and mouse T cell proliferation were determined similarly. FIG. 13A-13C showed the results of mouse allo-MLR demonstrating that the anti-PD-1 antibodies can enhance the function of mouse $CD4^+$ T cell. FIG. 13A showed anti-PD-1 antibodies increased IL-2 secretion in a dose-dependent manner. FIG. 13B showed anti-PD-1 antibodies increased IFN-γ secretion in a dose-dependent manner. FIG. 13C showed anti-PD-1 antibodies increased $CD4^+$ T cells proliferation in a dose-dependent manner.

7.2 Effect of Human Anti-PD-1 Antibodies on Cell Proliferation and Cytokine Production by Autologous Antigen Specific Immune Response In this assay, the $CD4^+$ T cells and DCs were from a same donor. Briefly, $CD4^+$ T cells were purified from PBMC and cultured in the presence of CMV pp65 peptide and low dose of IL-2 (20 U/mL), at the meanwhile, DCs were generated by culturing monocytes from the same donor's PBMC in GM-CSF and IL-4. After 5 days, the CMV pp65 peptide treated $CD4^+$ T cells were co-cultured with DCs pulsed with CMV pp65 peptide in the absence or presence of human anti-PD-1 antibodies or benchmark antibodies (as control). On day 5, 100 μL of supernatants were taken from each of cultures for IFN-γ measurement by ELISA as described above. The proliferation of CMV pp65-specific T cells was assessed by 3H-thymidine incorporation as described above.

Figure 14:
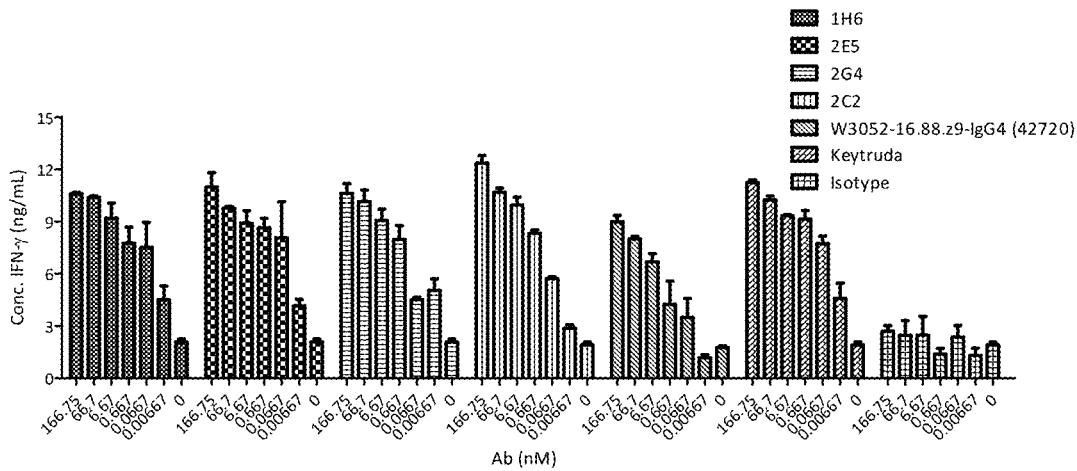
FIG. 14A-14B show the results of human allo-MLR demonstrating the anti-PD-1 antibodies can enhance the function of human CD4+ T cell.
Figure 14:
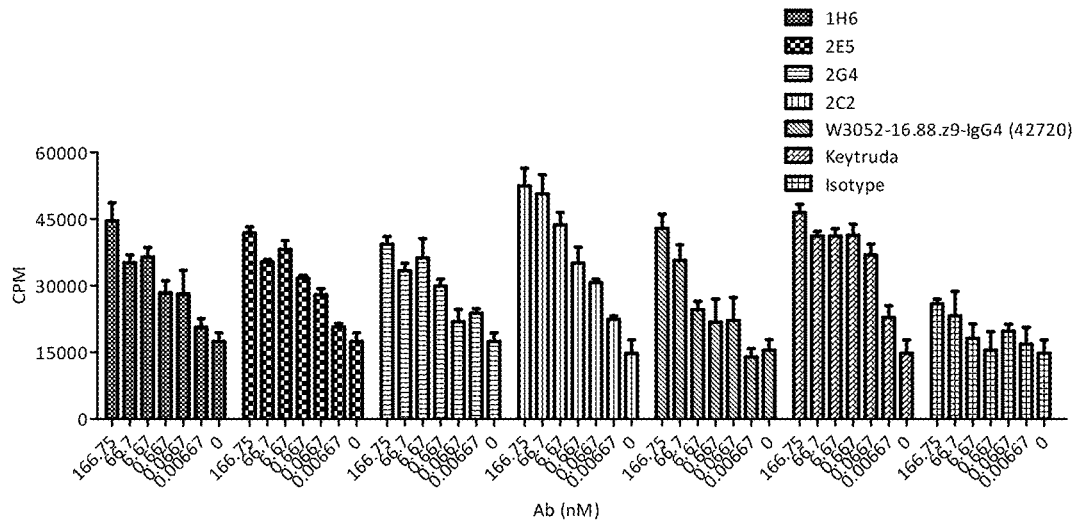

FIG. 14A-14B showed the results of human auto-MLR demonstrating the anti-PD-1 antibodies can enhance the function of human $CD4^+$ T cell. FIG. 14A showed anti-PD-1 antibodies increase IFN-γ secretion in a dose-dependent manner. FIG. 14B showed anti-PD-1 antibodies increase $CD4^+$ T cells proliferation in a dose-dependent manner.

7.3 Effect of Human Anti-PD-1 Antibodies on Regulatory T Cell (Tregs) Suppressive Function Tregs, a subpopulation of T cells, are a key immune modulator and play critical roles in maintaining self-tolerance. Increased numbers of $CD4^+CD25^+$ Tregs were found in patients with multiple cancers and associated with a poorer prognosis. To determine whether the anti-PD-1 antibodies affect the immune suppressive role of Tregs, we compared the T cell function in the presence of Tregs with or without anti-PD-1 antibody treatment. $CD4^+CD25^+$ and $CD4^+CD25^-$ T cells were separated using specific anti-CD25 microbeads (StemCell) per manufacture's instruction. Two thousand mature DCs, $1 \times 10^5$ $CD4^+CD25^-$ T cells, $1 \times 10^5$ Treg cells and PD-1 antibodies were incubated in 96-well plates. The plates were kept at 37° C. in a 5% $CO_2$ incubator for 5 days. IFN-γ production and $CD4^+CD25^-$ cells proliferation were tested as described above.

Figure 15:
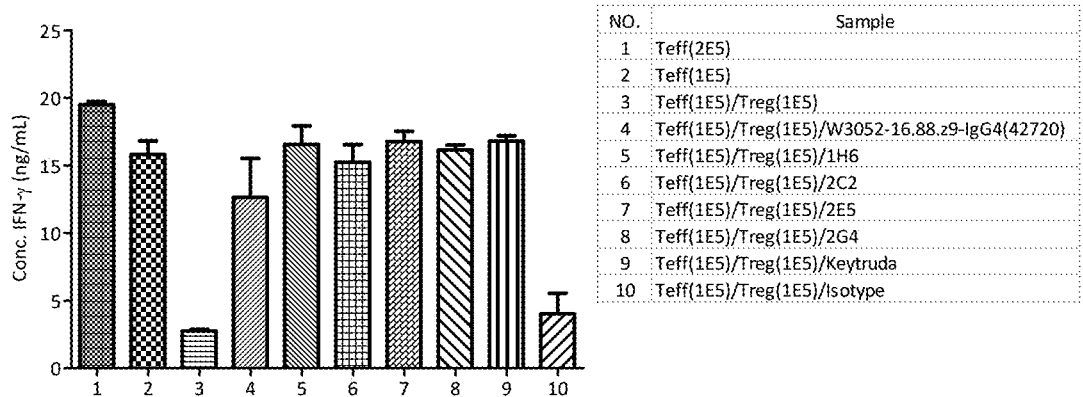
FIG. 15 demonstrates that the anti-PD-1 antibodies can reverse the suppressive function of Tregs.
Figure 15:
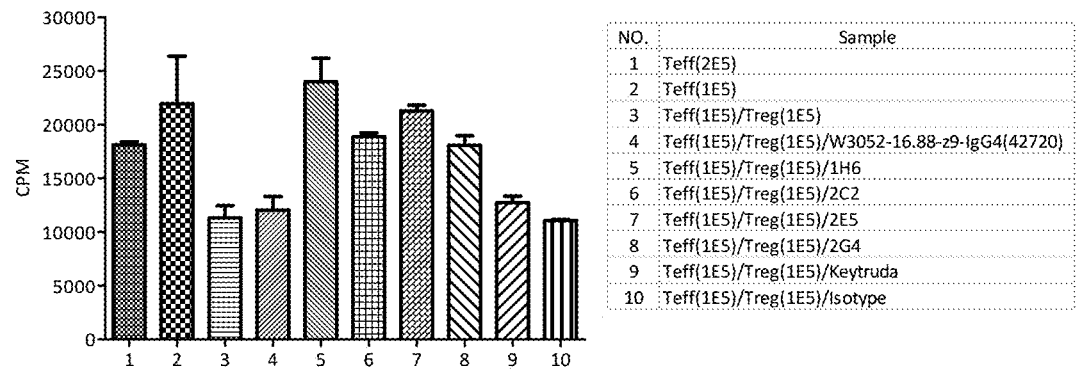

FIG. 15 demonstrates that the anti-PD-1 antibodies can reverse the suppressive function of Tregs. FIG. 15A showed anti-PD-1 antibodies can restore the IFN-γ secretion. FIG. 15B showed anti-PD-1 antibodies can restore the T-cell proliferation.

8. ADCC and CDC Test

PD-1 is expressed on variety of cell types. In order to minimize potential toxicity to healthy PD-1 positive cells, the anti-PD-1 antibodies were evaluated for their ability to mediate antibody-dependent cellular cytotoxicity (ADCC) and complement-dependent cytotoxicity (CDC).

8.1 ADCC Test

Human activated CD4+ T cells and various concentrations of PD-1 antibodies were pre-incubated in 96-well plate for 30 minutes, and then PBMCs were added at the effector/target ratio of 50:1. The plate was kept at 37° C. in a 5% $CO_2$ incubator for 6 hours. Target cell lysis was determined by LDH-based cytotoxicity detection kit (cat# Roche-11644793001). The absorbance at 492 nm was read using a microplate reader (Molecular Device). Herceptin-induced SK-Br-3 cell lysis was used as positive control.

Figure 16:
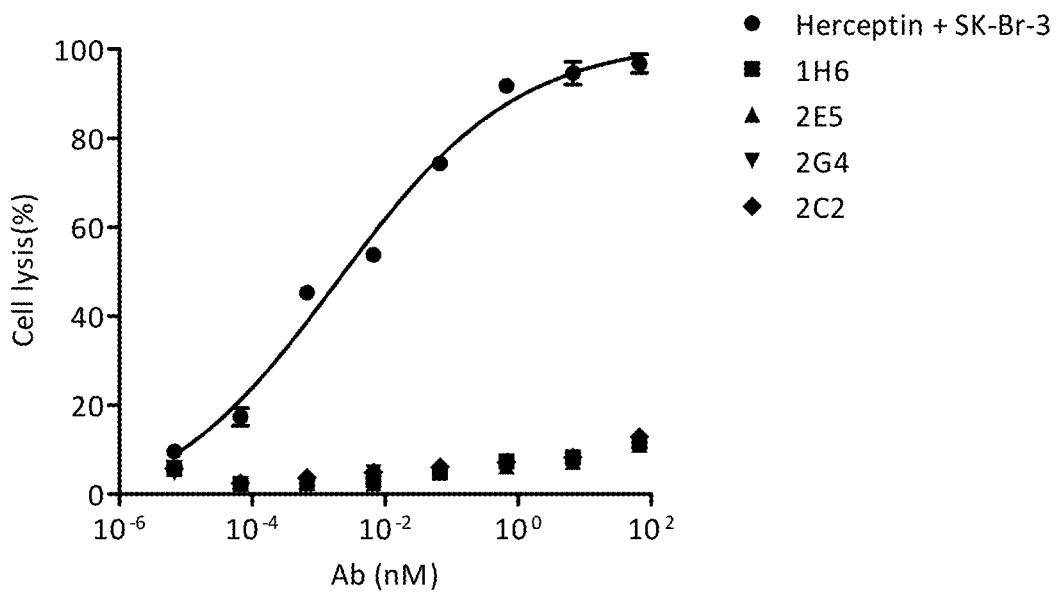
FIG. 16 shows the result of ADCC test demonstrating the anti-PD-1 antibodies do not mediate ADCC activity on activated CD4+ T cells.

FIG. 16 showed the result of ADCC test demonstrating the anti-PD-1 antibodies did not mediate ADCC activity on activated CD4+ T cells.

8.2 CDC Test

Human activated CD4+ T cells and various concentrations of PD-1 antibodies were mixed in 96-well plate. Human complement (Quidel-A112) was added at the dilution ratio of 1:50. The plate was kept at 37° C. in a 5% $CO_2$ incubator for 2 hours. Target cell lysis was determined by CellTiter-Glo. Rituxan®-induced Raji cell lysis was used as positive control. The luminescence was read using a microplate reader (Molecular Device).

Figure 17:
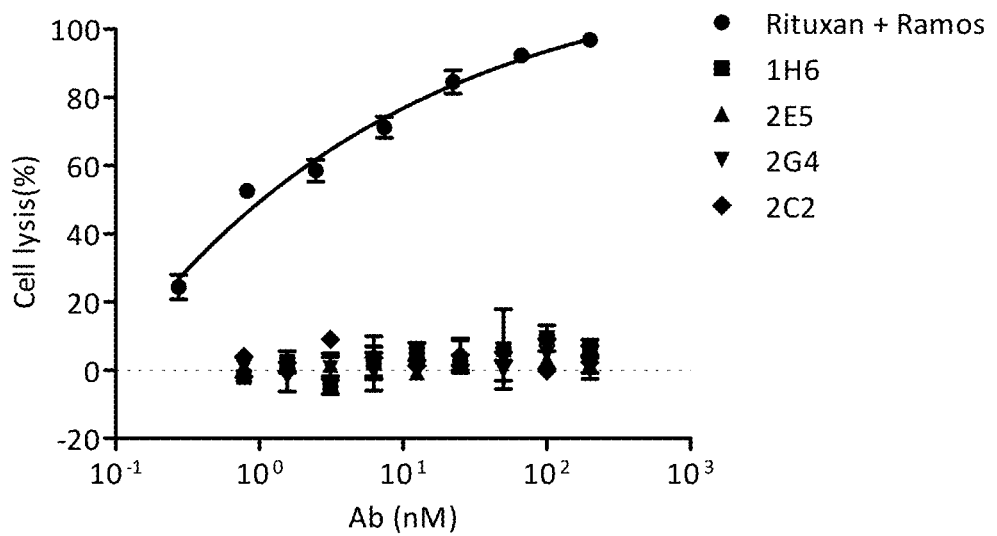
FIG. 17 shows the result of CDC test demonstrating the anti-PD-1 antibodies do not mediate CDC activity on activated CD4+ T cells.

FIG. 17 showed the result of CDC test demonstrating the anti-PD-1 antibodies did not mediate CDC activity on activated CD4+ T cells.

Example 5: Treatment of In Vivo Tumor Model Using Human Monoclonal Antibodies Against PD-1

1. Experimental Design

TABLE 10

Grouping and dosing regimen of the in vivo animal efficacy experiments of antibody 2E5

| group | N[1] | Treatment | Dose (mg/kg) | Dose-Volume Parameters (μl/g)[2] | Route of administration | Frequency of administration |
|---|---|---|---|---|---|---|
| 1 | 6 | Vehicle | — | 10 | IP | Q3D × 5 |
| 3 | 6 | 2E5 | 1 mg/kg | 10 | IP | Q3D × 5 |
| 4 | 6 | 2E5 | 3 mg/kg | 10 | IP | Q3D × 5 |
| 5 | 6 | 2E5 | 10 mg/kg | 10 | IP | Q3D × 5 |

Annotations:
[1]N: mice number in each group
[2]Dose-Volume: 10 μL/g according to the weight of mouse. If the weight loss exceeds 15%, the dosing regimen should be adjusted accordingly.

2. Methods 2.1 Cell Culture

Murine melanoma cell CloudmanS91 cell (ATCC-CCL-53.1) was cultured in vitro as monolayer, and the culture condition was F-12K medium plus 2.5% FBS and 15% horse serum, 100 U/mL penicillin, and 100 μg/mL streptomycin, incubate at 37° C. and 5% $CO_2$. The cells were digested using trypsin-EDTA and passaged twice a week routinely. Cells were harvested, counted, and then inoculated when approximately 80%-90% confluent and the number is as required.

2.2 Injection of Tumor Cells 0.1 mL ($5 \times 10^5$ cells) CloudmanS91 cells were inoculated subcutaneously in the right backside of each animal. When the mean of tumor volume had reached approximately 64 mm³, the administration started in groups. Grouping and dosing regimens were shown in Table 10.

2.3 Tumor Testing and Index

Experimental index is to investigate whether the tumor growth was inhibited, delayed or cured. Tumor diameters were measured with a caliper three times a week. Tumor volume is calculated using $V=0.5a \times b^2$, wherein a and b represents long and short diameters of the tumor, respectively.

Antitumor efficacy of the antibody was assessed by tumor growth inhibition TGI (%) or relative tumor proliferation rate T/C (%). TGI (%) reflected the rate of tumor growth inhibition. TGI (%) was calculated as follows:

TGI (%)=[(1−(average tumor volume at the end of administration in the treatment group−average tumor volume at the start of administration in the treatment group))/(average tumor volume at the end of treatment in the solvent control group−average tumor volume at the start of treatment in the solvent control group)]×100%.

Relative tumor proliferation rate T/C (%) was calculated as follows:

$$T/C \% = T_{RTV}/C_{RTV} \times 100\%$$

($T_{RTV}$: treatment group RTV; $C_{RTV}$: negative control group RTV). The relative tumor volume (RTV) was calculated according to the results of tumor measurements using $RTV=V_t/V_0$, wherein $V_0$ was average tumor volume at the time of grouping (i.e., $d_0$), $V_t$ was average tumor volume of a certain measurement; the data of $T_{RTV}$ and $C_{RTV}$ were taken on the same day.

T-C (days) reflected tumor growth delay index, T represented average days passed when the tumor had reached a predetermined volume in the treatment group (eg. 300 mm³), C represented the average days when tumors in the control group had reached the same volume.

Survival curves were plotted; animal survival time was defined as the time from the administration to animal deaths or the time when tumor volume had reached 2000 mm³. The median survival time (days) was calculated in each group. Increased life span (ILS) was calculated by comparison of the median survival times between the treated group and model control group and represented as a percentage over the lifetime of the model control group.

2.4 Statistical Analysis

The data including the average tumor volume at each time point in each group and standard error (SEM) were analyzed statistically (refer to Table 11 for specific data). The experiment was completed on day 37 after the administration; on day 13 after the administration, start sacrificing animals successively; and therefore the statistical analysis and evaluation for inter-group differences were based on the tumor volume on day 13 after initiation of administration. For comparisons between the two groups, data were analyzed using T-test; for comparisons among three or more groups, data were analyzed using one-way ANOVA. If statistically significant difference was found for F value, data were analyzed using Games-Howell test. If no statistically significant difference was found for F value, Dunnet (2-sided) test was then used for analysis. SPSS 17.0 was used for all data analysis. $p<0.05$ was considered as significant difference. Survival time was analyzed using Kaplan-Meier method with the Log-rank test.

3. Results 3.1 Mortality, Morbidity and Body Weight Changes

Animal's weight is as an indirect reference for measurement of drug toxicity. The impact of 2E5 on the weight of CloudmanS91 subcutaneous syngeneic xenograft female DBA/2 mice model was as shown in FIG. 18 and FIG. 19.

Figure 18:
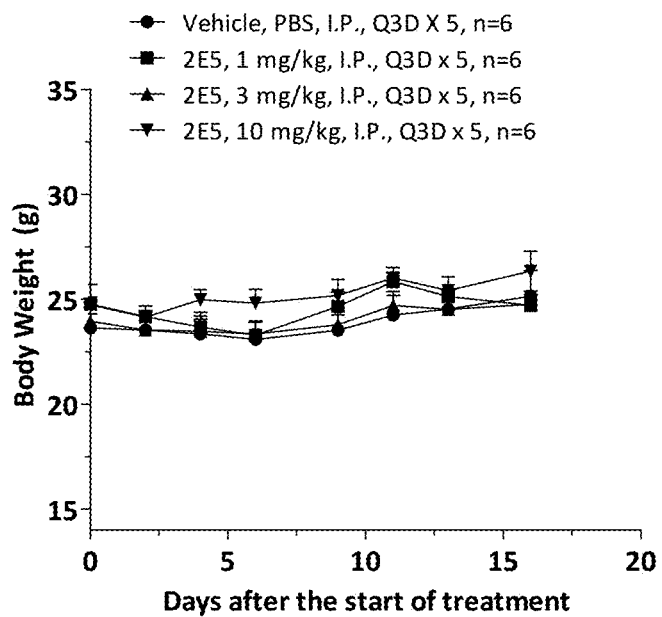
FIG. 18 shows body weight changes in syngeneic tumor nude mice model after treatment of 2E5. The data point represents the average body weight; error bars represent the standard error (SEM).
Figure 19:
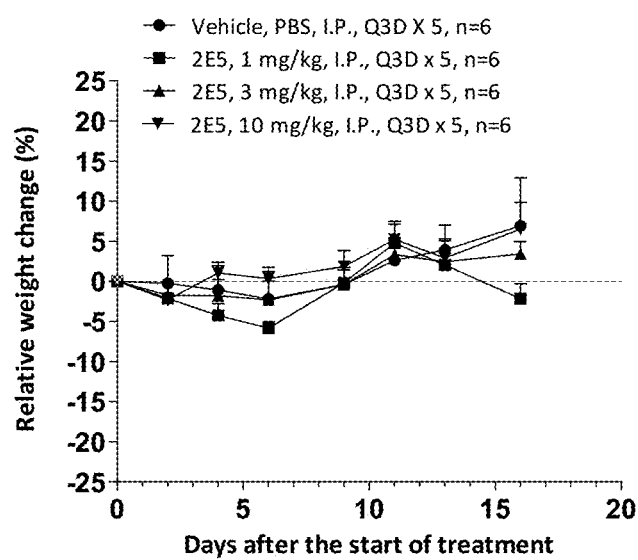
FIG. 19 shows relative weight changes (%). Relative change in body weight was calculated based on body weight at the start of the administration. The data point represents the average body weight; error bars represent the standard error (SEM).

In this model, all administration groups showed no significant weight loss (FIG. 18). Thus, 2E5 had no obvious toxicity in a mouse model of melanoma CloudmanS91.

3.2 Tumor Volume

Tumor volume in CloudmanS91 subcutaneously syngeneic xenograft female DBA/2 mouse model after 2E5 treatment was as shown in Table 11.

TABLE 11

Tumor volume at different times in each group

| Days | Vehicle | Tumor volume (mm$^3$)$^a$ | | |
|---|---|---|---|---|
| | | 2E5 1 mg/kg | 2E5 3 mg/kg | 2E5 10 mg/kg |
| 0$^b$ | 66 ± 9 | 65 ± 8 | 64 ± 8 | 63 ± 8 |
| 2 | 142 ± 23 | 129 ± 10 | 110 ± 10 | 94 ± 8 |
| 4 | 251 ± 39 | 231 ± 34 | 162 ± 9B | 143 ± 17 |
| 6 | 345 ± 65 | 339 ± 61 | 200 ± 13 | 197 ± 38 |
| 9 | 599 ± 66 | 597 ± 100 | 281 ± 38 | 291 ± 83 |
| 11 | 1,026 ± 173 | 943 ± 307 | 335 ± 66 | B475 ± 190 |
| 13 | 1,626 ± 262 | 1,089 ± 365 | 361 ± 81 | B614 ± 273 |

Annotations:
$^a$average ± SEM;
$^b$Days after administration.

3.3 Tumor Growth Curve

Figure 20:
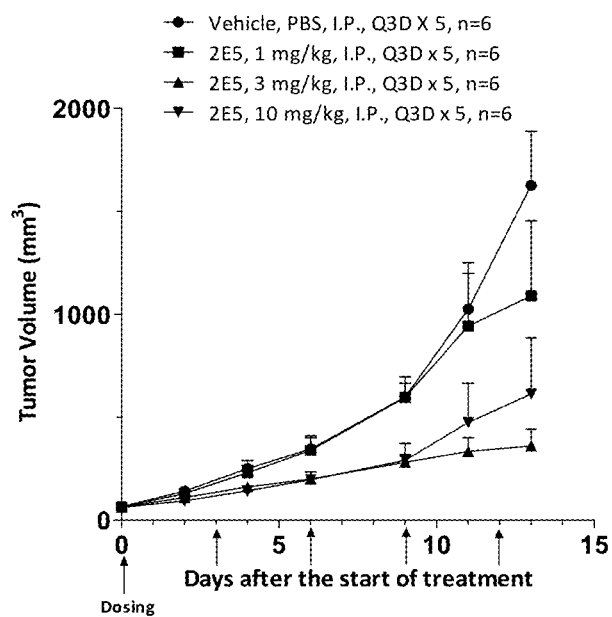
FIG. 20 shows tumor growth curve in CloudmanS91 syngeneic tumor nude mice model after treatment of 2E5. The data point represents the average body weight; error bars represent the standard error (SEM).

Tumor growth curve was shown in FIG. 20.

3.4 Antitumor Efficacy Evaluation

TABLE 12

Antitumor efficacy evaluation of 2E5 in CloudmanS91 Syngeneic tumor model (based on the tumor volume on day 13 after initiation of administration)

| group | Tumor volume (mm$^3$)$^a$ (Day 13) | T/C$^b$ (%) | XTGI$^b$ (%) | T-C (Days) (300 mm$^3$) | p value$^c$ |
|---|---|---|---|---|---|
| Vehicle | 1,626 ± 262 | — | — | — | — |
| 2E5 (1 mg/kg) | 1,089 ± 365 | 68.1 | 34.4 | 0 | 0.367 |
| 2E5 (3 mg/kg) | 361 ± 81 | 22.9 | 81.0 | 5 | 0.008 |
| 2E5 (10 mg/kg) | 614 ± 273 | 39.4 | 64.7 | 5 | 0.036 |

Annotations:
$^a$average ± SEM;
$^b$Tumor growth inhibition was calculated by T/C and TGI (TGI (%) = [1 − (T$_{13}$ − T$_0$)/(V$_{13}$ − V$_0$)] × 100);
$^c$p value was calculated by tumor volume.

3.5 Survival Curves

Figure 21:
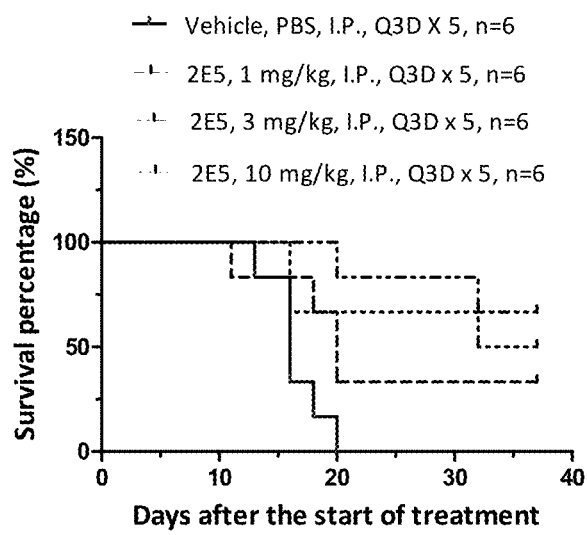
FIG. 21 shows survival curve in CloudmanS91 syngeneic tumor nude mice model after treatment of 2E5.

Survival curves in each group were shown in FIG. 21.

3.6 Survival Time

TABLE 13

Effect of 2E5 on survival of CloudmanS91 Syngeneic tumor model

| group | Median survival time (Days) | Prolonged survival (%) | Log Rank P value$^a$ |
|---|---|---|---|
| Vehicle | 16 | — | — |
| 2E5 1 mg/kg | 20 | 25 | 0.077 |
| 2E5 3 mg/kg | N/A$^b$ | N/A | 0.001 |
| 2E5 10 mg/kg | 32 | 100 | 0.022 |

Annotations:
$^a$p-value represented the comparison between the treatment group and the vehicle control group;
$^b$At the end of the experiment, in 3 mg/kg group (2E5), the survival rate was 66.7%.

4. Discussion

In this study, we have evaluated the in vivo efficacy of 2E5 in CloudmanS91 syngeneic tumor model. Tumor volume in each group at different time points were shown in Table 11, Table 12 and FIG. 20, survival time were shown in FIG. 21 and Table 13. On day 13 after administration, tumor volume of tumor-bearing mice in the solvent control group reached 1,626 mm$^3$. A weak inhibitory effect was observed in 1 mg/kg 2E5 group compared with the control group, and the tumor volume was 1,089 mm$^3$ (T/C=68.1%, TGI=34.4%, p=0.367), tumor growth delay was 0 days. A significant anti-tumor effect was observed in 3 mg/kg 2E5 group compared with the solvent control group, and the tumor volume was 361 mm$^3$ (T/C=22.9%, TGI=81.0%, p=0.008), tumor growth delay was 5 days. A significant anti-tumor effect was also observed in 10 mg/kg 2E5 group compared with the solvent control group, the tumor volume was 614 mm$^3$ (T/C=39.4%, TGI=64.7%, p=0.036), tumor growth delay was 5 days.

In the experiment, the median survival time of tumor-bearing mice in solvent control group was 16 days. Compared with the vehicle control group, the median survival time of tumor-bearing mice in 1 mg/kg 2E5 group was 20 days, survival was prolonged 25% (p=0.077); survival rate of tumor-bearing mice in 3 mg/kg 2E5 group was 66.7% (p=0.001). The median survival time of tumor-bearing mice in 10 mg/kg 2E5 group was 32 days, survival was prolonged 100% (p=0.022).

The changes in body weight of nude mice were shown in FIG. 19. Good tolerability of drug 2E5 has been found in all tumor-bearing mice, and no significant weight loss was observed in all treatment groups. In summary, in this experiment, significant anti-tumor effects were shown in both 3 mg/kg group and 10 mg/kg group for CloudmanS91 subcutaneous synergistic tumor model, which is not dose-dependent. Anti-tumor effect in 3 mg/kg group is better than that in 10 mg/kg group.

The description of the present invention has been made above by the examples. However, it is understood by the skilled in the art that the present invention is not limited to the examples. The invention may be embodied in other specific forms without departing form the spirit or essential characteristics thereof. Scope of the invention is thus indicated by the appended claims rather than by the foregoing description, and all changes that come within the meaning and range of equivalency of the claims are intended to be embraced therein.

What is claimed is:

1. An antibody, or antigen-binding fragment thereof, wherein the antibody or antigen binding fragment thereof comprises:
   a) a heavy chain variable region CDR1 sequence comprising SEQ ID NO: 10, a heavy chain variable region CDR2 sequence comprising SEQ ID NO: 11, and a heavy chain variable region CDR3 sequence comprising SEQ ID NO: 13; and a light chain variable region CDR1 sequence comprising SEQ ID NO: 14, a light chain variable region CDR2 sequence comprising SEQ ID NO: 19, and a light chain variable region CDR3 sequence comprising SEQ ID NO: 21; or
   b) a heavy chain variable region CDR1 sequence comprising SEQ ID NO: 10, a heavy chain variable region CDR2 sequence comprising SEQ ID NO: 11, and a heavy chain variable region CDR3 sequence comprising SEQ ID NO: 13; and a light chain variable region CDR1 sequence comprising SEQ ID NO: 15, a light chain variable region CDR2 sequence comprising SEQ ID NO: 19, and a light chain variable region CDR3 sequence comprising SEQ ID NO: 21; or
   c) a heavy chain variable region CDR1 sequence comprising SEQ ID NO: 10, a heavy chain variable region CDR2 sequence comprising SEQ ID NO: 11, and a heavy chain variable region CDR3 sequence comprising SEQ ID NO: 13; and a light chain variable region CDR1 sequence comprising SEQ ID NO: 16, a light chain variable region CDR2 sequence comprising SEQ ID NO: 19, and a light chain variable region CDR3 sequence comprising SEQ ID NO: 21; or
   d) a heavy chain variable region CDR1 sequence comprising SEQ ID NO: 10, a heavy chain variable region CDR2 sequence comprising SEQ ID NO: 11, and a heavy chain variable region CDR3 sequence comprising SEQ ID NO: 13; and a light chain variable region CDR1 sequence comprising SEQ ID NO: 17, a light chain variable region CDR2 sequence comprising SEQ ID NO: 19, and a light chain variable region CDR3 sequence comprising SEQ ID NO: 21; or e) a heavy chain variable region CDR1 sequence comprising SEQ ID NO: 10, a heavy chain variable region CDR2 sequence comprising SEQ ID NO: 11, and a heavy chain variable region CDR3 sequence comprising SEQ ID NO: 13; and a light chain variable region CDR1 sequence comprising SEQ ID NO: 17, a light chain variable region CDR2 sequence comprising SEQ ID NO: 19, and a light chain variable region CDR3 sequence comprising SEQ ID NO: 22; or f) a heavy chain variable region CDR1 sequence comprising SEQ ID NO: 10, a heavy chain variable region CDR2 sequence comprising SEQ ID NO: 11, and a heavy chain variable region CDR3 sequence comprising SEQ ID NO: 12; and a light chain variable region CDR1 sequence comprising SEQ ID NO: 14, a light chain variable region CDR2 sequence comprising SEQ ID NO: 19, and a light chain variable region CDR3 sequence comprising SEQ ID NO: 21; or g) a heavy chain variable region CDR1 sequence comprising SEQ ID NO: 10, a heavy chain variable region CDR2 sequence comprising SEQ ID NO: 11, and a heavy chain variable region CDR3 sequence comprising SEQ ID NO: 12; and a light chain variable region CDR1 sequence comprising SEQ ID NO: 16, a light chain variable region CDR2 sequence comprising SEQ ID NO: 19, and a light chain variable region CDR3 sequence comprising SEQ ID NO: 21; or h) a heavy chain variable region CDR1 sequence comprising SEQ ID NO: 10, a heavy chain variable region CDR2 sequence comprising SEQ ID NO: 11, and a heavy chain variable region CDR3 sequence comprising SEQ ID NO: 12; and a light chain variable region CDR1 sequence comprising SEQ ID NO: 17, a light chain variable region CDR2 sequence comprising SEQ ID NO: 19, and a light chain variable region CDR3 sequence comprising SEQ ID NO: 21; or i) a heavy chain variable region CDR1 sequence comprising SEQ ID NO: 10, a heavy chain variable region CDR2 sequence comprising SEQ ID NO: 11, and a heavy chain variable region CDR3 sequence comprising SEQ ID NO: 12; and a light chain variable region CDR1 sequence comprising SEQ ID NO: 18, a light chain variable region CDR2 sequence comprising SEQ ID NO: 19, and a light chain variable region CDR3 sequence comprising SEQ ID NO: 23; or j) a heavy chain variable region CDR1 sequence comprising SEQ ID NO: 10, a heavy chain variable region CDR2 sequence comprising SEQ ID NO: 11, and a heavy chain variable region CDR3 sequence comprising SEQ ID NO: 12; and a light chain variable region CDR1 sequence comprising SEQ ID NO: 18, a light chain variable region CDR2 sequence comprising SEQ ID NO: 19, and a light chain variable region CDR3 sequence comprising SEQ ID NO: 20;

wherein the antibody specifically binds to PD-1.

2. The antibody of claim 1, wherein the antibody is chimeric or humanized or human antibody.

3. The antibody of claim 1, wherein the antibody exhibits at least one of the following properties:

(a) binds to human PD-1 with a $K_D$ of 2.15E-10 M or less and to mouse PD-1 with a $K_D$ of 1.67E-08 M or less;
(b) does not bind to human CD28 or CTLA-4;
(c) increases T-cell proliferation;
(d) increases interferon-gamma production; or
(e) increases interleukin-2 secretion.

4. A nucleic acid molecule encoding the antibody, or the antigen binding fragment of claim 1.

5. A cloning or expression vector comprising the nucleic acid molecule of claim 4.

6. A host cell comprising one or more cloning or expression vectors of claim 5.

7. A process for the production of the antibody of claim 1, comprising culturing the host cell of claim 6 and isolating the antibody.

8. A transgenic rat comprising human immunoglobulin heavy and light chain transgenes, wherein the mouse expresses the antibody of claim 1.

9. A hybridoma prepared from the rat of claim 8, wherein the hybridoma produces said antibody.

10. A pharmaceutical composition comprising the antibody, or the antigen binding fragment of claim 1, and one or more of a pharmaceutically acceptable excipient, diluent or carrier.

11. An immunoconjugate comprising the antibody, or antigen-binding fragment thereof, according to claim 1, linked to a therapeutic agent.

12. A pharmaceutical composition comprising the immunoconjugate of claim 11 and a pharmaceutically acceptable excipient, diluent or carrier.

13. A method of modulating an immune response in a subject comprising administering to the subject the antibody, or antigen binding fragment of claim 1.

14. A method of inhibiting growth of tumor cells in a subject, comprising administering to the subject a therapeutically effective amount of the antibody, or the antigen-binding fragment of claim 1 to inhibit growth of the tumor cells.

15. The method of claim 14, wherein the tumor cells are of a cancer selected from a group consisting of melanoma, renal cancer, prostate cancer, breast cancer, colon cancer, lung cancer, bone cancer, pancreatic cancer, skin cancer, cancer of the head or neck, cutaneous or intraocular malignant melanoma, uterine cancer, ovarian cancer, and rectal cancer.

16. The method of claim 14, wherein the antibody is a chimeric antibody or humanized antibody.

17. The antibody or the antigen binding fragment thereof of claim 1, wherein the antibody:

(a) binds to human PD-1 with a $K_D$ of 2.15E-10 M or less; and
(b) binds to mouse PD-1 with a $K_D$ of 1.67E-08 M or less.

18. The antibody or antigen binding fragment thereof of claim 1, comprising:

(a) a variable region of a heavy chain having an amino acid sequence selected from the group consisting of SEQ ID NOs: 1 and 2; and
(b) a variable region of a light chain having an amino acid sequence selected from the group consisting of SEQ ID NOs: 3, 4, 5, 6, 7, 8 and 9.

* * * * *

UNITED STATES PATENT AND TRADEMARK OFFICE
CERTIFICATE OF CORRECTION

| | | |
|---|---|---|
| PATENT NO. | : 11,414,487 B2 | Page 1 of 1 |
| APPLICATION NO. | : 16/333993 | |
| DATED | : August 16, 2022 | |
| INVENTOR(S) | : Zheng et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 276 days.

Signed and Sealed this
Eleventh Day of February, 2025

Coke Morgan Stewart
*Acting Director of the United States Patent and Trademark Office*

SEQUENCE LISTING

<160> NUMBER OF SEQ ID NOS: 24

<210> SEQ ID NO 1
<211> LENGTH: 115
<212> TYPE: PRT

```
<213> ORGANISM: Artificial Sequence
<220> FEATURE:
<223> OTHER INFORMATION: Protein

<400> SEQUENCE: 1

Gln Val Gln Leu Val Gln Ser Gly Ala Glu Val Lys Lys Pro Gly Ser
1               5                   10                  15

Ser Val Lys Val Ser Cys Lys Ala Ser Gly Phe Thr Phe Thr Thr Tyr
            20                  25                  30

Tyr Ile Ser Trp Val Arg Gln Ala Pro Gly Gln Gly Leu Glu Tyr Leu
        35                  40                  45

Gly Tyr Ile Asn Met Gly Ser Gly Gly Thr Asn Tyr Asn Glu Lys Phe
    50                  55                  60

Lys Gly Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Ile Leu Gly Tyr Phe Asp Tyr Trp Gly Gln Gly Thr Met Val Thr
            100                 105                 110

Val Ser Ser
        115

<210> SEQ ID NO 2
<211> LENGTH: 115
<212> TYPE: PRT
<213> ORGANISM: Artificial Sequence
<220> FEATURE:
<223> OTHER INFORMATION: Protein

<400> SEQUENCE: 2

Gln Val Gln Leu Val Gln Ser Gly Ala Glu Val Lys Lys Pro Gly Ser
1               5                   10                  15

Ser Val Lys Val Ser Cys Lys Ala Ser Gly Phe Thr Phe Thr Thr Tyr
            20                  25                  30

Tyr Ile Ser Trp Val Arg Gln Ala Pro Gly Gln Gly Leu Glu Tyr Leu
        35                  40                  45

Gly Tyr Ile Asn Met Gly Ser Gly Gly Thr Asn Tyr Asn Glu Lys Phe
    50                  55                  60

Lys Gly Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Ile Ile Gly Tyr Phe Asp Tyr Trp Gly Gln Gly Thr Met Val Thr
            100                 105                 110

Val Ser Ser
        115

<210> SEQ ID NO 3
<211> LENGTH: 112
<212> TYPE: PRT
<213> ORGANISM: Artificial Sequence
<220> FEATURE:
<223> OTHER INFORMATION: Protein

<400> SEQUENCE: 3

Asp Val Val Met Thr Gln Ser Pro Leu Ser Leu Pro Val Thr Leu Gly
1               5                   10                  15

Gln Pro Ala Ser Ile Ser Cys Arg Ser Ser Gln Ser Leu Leu Asp Ser
            20                  25                  30
```

Asp Gly Gly Thr Tyr Leu Tyr Trp Phe Gln Gln Arg Pro Gly Gln Ser
            35                  40                  45

Pro Arg Arg Leu Ile Tyr Leu Val Ser Thr Leu Gly Ser Gly Val Pro
 50                  55                  60

Asp Arg Phe Ser Gly Ser Gly Ser Gly Thr Asp Phe Thr Leu Lys Ile
 65                  70                  75                  80

Ser Arg Val Glu Ala Glu Asp Val Gly Val Tyr Tyr Cys Met Gln Leu
                85                  90                  95

Thr His Trp Pro Tyr Thr Phe Gly Gln Gly Thr Lys Leu Glu Ile Lys
            100                 105                 110

<210> SEQ ID NO 4
<211> LENGTH: 112
<212> TYPE: PRT
<213> ORGANISM: Artificial Sequence
<220> FEATURE:
<223> OTHER INFORMATION: Protein

<400> SEQUENCE: 4

Asp Val Val Met Thr Gln Ser Pro Leu Ser Leu Pro Val Thr Leu Gly
 1               5                  10                  15

Gln Pro Ala Ser Ile Ser Cys Arg Ser Ser Gln Ser Leu Leu Asp Ser
                20                  25                  30

Asp Gly Ser Thr Tyr Leu Tyr Trp Phe Gln Gln Arg Pro Gly Gln Ser
            35                  40                  45

Pro Arg Arg Leu Ile Tyr Leu Val Ser Thr Leu Gly Ser Gly Val Pro
 50                  55                  60

Asp Arg Phe Ser Gly Ser Gly Ser Gly Thr Asp Phe Thr Leu Lys Ile
 65                  70                  75                  80

Ser Arg Val Glu Ala Glu Asp Val Gly Val Tyr Tyr Cys Met Gln Leu
                85                  90                  95

Thr His Trp Pro Tyr Thr Phe Gly Gln Gly Thr Lys Leu Glu Ile Lys
            100                 105                 110

<210> SEQ ID NO 5
<211> LENGTH: 112
<212> TYPE: PRT
<213> ORGANISM: Artificial Sequence
<220> FEATURE:
<223> OTHER INFORMATION: Protein

<400> SEQUENCE: 5

Asp Val Val Met Thr Gln Ser Pro Leu Ser Leu Pro Val Thr Leu Gly
 1               5                  10                  15

Gln Pro Ala Ser Ile Ser Cys Arg Ser Ser Gln Ser Leu Leu Asp Ser
                20                  25                  30

Asp Gly Ala Thr Tyr Leu Tyr Trp Phe Gln Gln Arg Pro Gly Gln Ser
            35                  40                  45

Pro Arg Arg Leu Ile Tyr Leu Val Ser Thr Leu Gly Ser Gly Val Pro
 50                  55                  60

Asp Arg Phe Ser Gly Ser Gly Ser Gly Thr Asp Phe Thr Leu Lys Ile
 65                  70                  75                  80

Ser Arg Val Glu Ala Glu Asp Val Gly Val Tyr Tyr Cys Met Gln Leu
                85                  90                  95

Thr His Trp Pro Tyr Thr Phe Gly Gln Gly Thr Lys Leu Glu Ile Lys
            100                 105                 110

```
<210> SEQ ID NO 6
<211> LENGTH: 112
<212> TYPE: PRT
<213> ORGANISM: Artificial Sequence
<220> FEATURE:
<223> OTHER INFORMATION: Protein

<400> SEQUENCE: 6

Asp Val Val Met Thr Gln Ser Pro Leu Ser Leu Pro Val Thr Leu Gly
1               5                   10                  15

Gln Pro Ala Ser Ile Ser Cys Arg Ser Ser Gln Ser Leu Leu Asp Ser
            20                  25                  30

Asp Gly Asn Thr Tyr Leu Tyr Trp Phe Gln Gln Arg Pro Gly Gln Ser
        35                  40                  45

Pro Arg Arg Leu Ile Tyr Leu Val Ser Thr Leu Gly Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Leu
                85                  90                  95

Thr His Trp Pro Tyr Thr Phe Gly Gln Gly Thr Lys Leu Glu Ile Lys
            100                 105                 110

<210> SEQ ID NO 7
<211> LENGTH: 112
<212> TYPE: PRT
<213> ORGANISM: Artificial Sequence
<220> FEATURE:
<223> OTHER INFORMATION: Protein

<400> SEQUENCE: 7

Asp Val Val Met Thr Gln Ser Pro Leu Ser Leu Pro Val Thr Leu Gly
1               5                   10                  15

Gln Pro Ala Ser Ile Ser Cys Arg Ser Ser Gln Ser Leu Leu Asp Ser
            20                  25                  30

Asp Gly Asn Thr Tyr Leu Tyr Trp Phe Gln Gln Arg Pro Gly Gln Ser
        35                  40                  45

Pro Arg Arg Leu Ile Tyr Leu Val Ser Thr Leu Gly Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Leu
                85                  90                  95

Thr His Ala Pro Tyr Thr Phe Gly Gln Gly Thr Lys Leu Glu Ile Lys
            100                 105                 110

<210> SEQ ID NO 8
<211> LENGTH: 112
<212> TYPE: PRT
<213> ORGANISM: Artificial Sequence
<220> FEATURE:
<223> OTHER INFORMATION: Protein

<400> SEQUENCE: 8

Asp Val Val Met Thr Gln Ser Pro Leu Ser Leu Pro Val Thr Leu Gly
1               5                   10                  15

Gln Pro Ala Ser Ile Ser Cys Arg Ser Ser Gln Ser Leu Leu Asp Ser
            20                  25                  30

Asp Gly Gln Thr Tyr Leu Tyr Trp Phe Gln Gln Arg Pro Gly Gln Ser
        35                  40                  45
```

```
Pro Arg Arg Leu Ile Tyr Leu Val Ser Thr Leu Gly Ser Gly Val Pro
        50                  55                  60

Asp Arg Phe Ser Gly Ser Gly Ser Gly Thr Asp Phe Thr Leu Lys Ile
 65                 70                  75                  80

Ser Arg Val Glu Ala Glu Asp Val Gly Val Tyr Tyr Cys Met Gln Leu
                85                  90                  95

Thr His Glu Pro Tyr Thr Phe Gly Gln Gly Thr Lys Leu Glu Ile Lys
            100                 105                 110
```

<210> SEQ ID NO 9
<211> LENGTH: 112
<212> TYPE: PRT
<213> ORGANISM: Artificial Sequence
<220> FEATURE:
<223> OTHER INFORMATION: Protein

<400> SEQUENCE: 9

```
Asp Val Val Met Thr Gln Ser Pro Leu Ser Leu Pro Val Thr Leu Gly
 1               5                  10                  15

Gln Pro Ala Ser Ile Ser Cys Arg Ser Gln Ser Leu Leu Asp Ser
             20                  25                  30

Asp Gly Gln Thr Tyr Leu Tyr Trp Phe Gln Gln Arg Pro Gly Gln Ser
             35                  40                  45

Pro Arg Arg Leu Ile Tyr Leu Val Ser Thr Leu Gly Ser Gly Val Pro
        50                  55                  60

Asp Arg Phe Ser Gly Ser Gly Ser Gly Thr Asp Phe Thr Leu Lys Ile
 65                 70                  75                  80

Ser Arg Val Glu Ala Glu Asp Val Gly Val Tyr Tyr Cys Met Gln Leu
                85                  90                  95

Thr His Glu Asn Tyr Thr Phe Gly Gln Gly Thr Lys Leu Glu Ile Lys
            100                 105                 110
```

<210> SEQ ID NO 10
<211> LENGTH: 5
<212> TYPE: PRT
<213> ORGANISM: Artificial Sequence
<220> FEATURE:
<223> OTHER INFORMATION: Protein

<400> SEQUENCE: 10

```
Thr Tyr Tyr Ile Ser
 1               5
```

<210> SEQ ID NO 11
<211> LENGTH: 17
<212> TYPE: PRT
<213> ORGANISM: Artificial Sequence
<220> FEATURE:
<223> OTHER INFORMATION: Protein

<400> SEQUENCE: 11

```
Tyr Ile Asn Met Gly Ser Gly Gly Thr Asn Tyr Asn Glu Lys Phe Lys
 1               5                  10                  15

Gly
```

<210> SEQ ID NO 12
<211> LENGTH: 6
<212> TYPE: PRT
<213> ORGANISM: Artificial Sequence
<220> FEATURE:
<223> OTHER INFORMATION: Protein

<400> SEQUENCE: 12

Leu Gly Tyr Phe Asp Tyr
1               5

<210> SEQ ID NO 13
<211> LENGTH: 6
<212> TYPE: PRT
<213> ORGANISM: Artificial Sequence
<220> FEATURE:
<223> OTHER INFORMATION: Protein

<400> SEQUENCE: 13

Ile Gly Tyr Phe Asp Tyr
1               5

<210> SEQ ID NO 14
<211> LENGTH: 16
<212> TYPE: PRT
<213> ORGANISM: Artificial Sequence
<220> FEATURE:
<223> OTHER INFORMATION: Protein

<400> SEQUENCE: 14

Arg Ser Ser Gln Ser Leu Leu Asp Ser Asp Gly Gly Thr Tyr Leu Tyr
1               5                   10                  15

<210> SEQ ID NO 15
<211> LENGTH: 16
<212> TYPE: PRT
<213> ORGANISM: Artificial Sequence
<220> FEATURE:
<223> OTHER INFORMATION: Protein

<400> SEQUENCE: 15

Arg Ser Ser Gln Ser Leu Leu Asp Ser Asp Gly Ser Thr Tyr Leu Tyr
1               5                   10                  15

<210> SEQ ID NO 16
<211> LENGTH: 16
<212> TYPE: PRT
<213> ORGANISM: Artificial Sequence
<220> FEATURE:
<223> OTHER INFORMATION: Protein

<400> SEQUENCE: 16

Arg Ser Ser Gln Ser Leu Leu Asp Ser Asp Gly Ala Thr Tyr Leu Tyr
1               5                   10                  15

<210> SEQ ID NO 17
<211> LENGTH: 16
<212> TYPE: PRT
<213> ORGANISM: Artificial Sequence
<220> FEATURE:
<223> OTHER INFORMATION: Protein

<400> SEQUENCE: 17

Arg Ser Ser Gln Ser Leu Leu Asp Ser Asp Gly Asn Thr Tyr Leu Tyr
1               5                   10                  15

<210> SEQ ID NO 18
<211> LENGTH: 16
<212> TYPE: PRT
<213> ORGANISM: Artificial Sequence
<220> FEATURE:
<223> OTHER INFORMATION: Protein

<400> SEQUENCE: 18

Arg Ser Ser Gln Ser Leu Leu Asp Ser Asp Gly Gln Thr Tyr Leu Tyr
1               5                   10                  15

<210> SEQ ID NO 19
<211> LENGTH: 7
<212> TYPE: PRT
<213> ORGANISM: Artificial Sequence
<220> FEATURE:
<223> OTHER INFORMATION: Protein

<400> SEQUENCE: 19

Leu Val Ser Thr Leu Gly Ser
1               5

<210> SEQ ID NO 20
<211> LENGTH: 9
<212> TYPE: PRT
<213> ORGANISM: Artificial Sequence
<220> FEATURE:
<223> OTHER INFORMATION: Protein

<400> SEQUENCE: 20

Met Gln Leu Thr His Glu Asn Tyr Thr
1               5

<210> SEQ ID NO 21
<211> LENGTH: 9
<212> TYPE: PRT
<213> ORGANISM: Artificial Sequence
<220> FEATURE:
<223> OTHER INFORMATION: Protein

<400> SEQUENCE: 21

Met Gln Leu Thr His Trp Pro Tyr Thr
1               5

<210> SEQ ID NO 22
<211> LENGTH: 9
<212> TYPE: PRT
<213> ORGANISM: Artificial Sequence
<220> FEATURE:
<223> OTHER INFORMATION: Protein

<400> SEQUENCE: 22

Met Gln Leu Thr His Ala Pro Tyr Thr
1               5

<210> SEQ ID NO 23
<211> LENGTH: 9
<212> TYPE: PRT
<213> ORGANISM: Artificial Sequence
<220> FEATURE:
<223> OTHER INFORMATION: Protein

<400> SEQUENCE: 23

Met Gln Leu Thr His Glu Pro Tyr Thr
1               5

<210> SEQ ID NO 24
<211> LENGTH: 288
<212> TYPE: PRT
<213> ORGANISM: Artificial Sequence
<220> FEATURE:
<223> OTHER INFORMATION: Protein

<400> SEQUENCE: 24

-continued

```
Met Gln Ile Pro Gln Ala Pro Trp Pro Val Val Trp Ala Val Leu Gln
1               5                   10                  15

Leu Gly Trp Arg Pro Gly Trp Phe Leu Asp Ser Pro Asp Arg Pro Trp
                20                  25                  30

Asn Pro Pro Thr Phe Ser Pro Ala Leu Leu Val Val Thr Glu Gly Asp
            35                  40                  45

Asn Ala Thr Phe Thr Cys Ser Phe Ser Asn Thr Ser Glu Ser Phe Val
50                      55                  60

Leu Asn Trp Tyr Arg Met Ser Pro Ser Asn Gln Thr Asp Lys Leu Ala
65                  70                  75                  80

Ala Phe Pro Glu Asp Arg Ser Gln Pro Gly Gln Asp Cys Arg Phe Arg
                85                  90                  95

Val Thr Gln Leu Pro Asn Gly Arg Asp Phe His Met Ser Val Val Arg
                100                 105                 110

Ala Arg Arg Asn Asp Ser Gly Thr Tyr Leu Cys Gly Ala Ile Ser Leu
            115                 120                 125

Ala Pro Lys Ala Gln Ile Lys Glu Ser Leu Arg Ala Glu Leu Arg Val
    130                 135                 140

Thr Glu Arg Arg Ala Glu Val Pro Thr Ala His Pro Ser Pro Ser Pro
145                 150                 155                 160

Arg Pro Ala Gly Gln Phe Gln Thr Leu Val Val Gly Val Val Gly Gly
                165                 170                 175

Leu Leu Gly Ser Leu Val Leu Leu Val Trp Val Leu Ala Val Ile Cys
                180                 185                 190

Ser Arg Ala Ala Arg Gly Thr Ile Gly Ala Arg Arg Thr Gly Gln Pro
            195                 200                 205

Leu Lys Glu Asp Pro Ser Ala Val Pro Val Phe Ser Val Asp Tyr Gly
    210                 215                 220

Glu Leu Asp Phe Gln Trp Arg Glu Lys Thr Pro Glu Pro Pro Val Pro
225                 230                 235                 240

Cys Val Pro Glu Gln Thr Glu Tyr Ala Thr Ile Val Phe Pro Ser Gly
                245                 250                 255

Met Gly Thr Ser Ser Pro Ala Arg Arg Gly Ser Ala Asp Gly Pro Arg
            260                 265                 270

Ser Ala Gln Pro Leu Arg Pro Glu Asp Gly His Cys Ser Trp Pro Leu
            275                 280                 285
```